US006356785B1

(12) United States Patent
Snyder et al.

(10) Patent No.: US 6,356,785 B1
(45) Date of Patent: Mar. 12, 2002

(54) EXTERNAL DEFIBRILLATOR WITH CPR PROMPTS AND ACLS PROMPTS AND METHODS OF USE

(76) Inventors: Cecily Anne Snyder, 545 Arguello St., #4, San Francisco, CA (US) 94118; Bradford E. Gliner, 4368 230th Way SE., Ilssaquah, WA (US) 98029; David E. Snyder, 353 Wallace Way NE., #15, Bainbridge Island, WA (US) 98110

(*) Notice: Subject to any disclaimer, the term of this patent is extended or adjusted under 35 U.S.C. 154(b) by 0 days.

(21) Appl. No.: 09/331,998
(22) PCT Filed: Oct. 21, 1998
(86) PCT No.: PCT/US98/22194
  § 371 Date: Aug. 18, 1999
  § 102(e) Date: Aug. 18, 1999
(87) PCT Pub. No.: WO99/24114
  PCT Pub. Date: May 20, 1999

Related U.S. Application Data

(63) Continuation-in-part of application No. 08/994,495, filed on Dec. 19, 1997, now abandoned, which is a continuation-in-part of application No. 08/965,347, filed on Nov. 6, 1997, now abandoned.

(51) Int. Cl.[7] ................................................ A61N 1/39
(52) U.S. Cl. ........................................................ 607/5
(58) Field of Search ...................... 607/3–5; 601/41–44

(56) References Cited

U.S. PATENT DOCUMENTS

| | | |
|---|---|---|
| 3,520,071 A | 7/1970 | Abrahamson et al. |
| 4,016,540 A | 4/1977 | Hyatt |
| 4,181,134 A | 1/1980 | Mason et al. |
| 4,370,983 A | 2/1983 | Lichtenstein |
| 4,420,813 A | 12/1983 | Inoue et al. |
| 4,451,158 A | 5/1984 | Selwyn et al. |
| 4,457,312 A | 7/1984 | Ornato et al. |
| 4,489,387 A | 12/1984 | Lamb et al. |

(List continued on next page.)

FOREIGN PATENT DOCUMENTS

| | | |
|---|---|---|
| WO | WO 00/27464 | 5/2000 |
| WO | WO 00/30712 | 6/2000 |

OTHER PUBLICATIONS

Product Brochure from CPR Prompt® Rescue Aid, "Model I (Wall Mount) and Model II (Soft Case) Instructions," County Line Limited, Health and Safety Products Division, (no date).
Product Brochure from CPR Prompt® Rescue and Practice Aid, "Use and Care Book, Model CPR100," County Line Limited, LLC, 1996.

(List continued on next page.)

Primary Examiner—Jeffrey R. Jastrzab

(57) ABSTRACT

This invention relates generally to defibrillators and, in particular, to a defibrillator with a built in CPR ("CPR") prompt system. The invention also relates generally to a defibrillator with a built-in Advanced Cardiac Life Support ("ACLS") prompt system. Defibrillators include manual defibrillator, automatic or semiautomatic external defibrillators ("AEDs") and defibrillator trainers. More specifically, this invention is directed to a defibrillator system capable of generating audible prompts and/or visual prompts through an audible prompt generator and a visual prompt generator, wherein the defibrillator instructs a rescuer on performing CPR or ACLS. The instructions are controlled through a prompt generator and may be audible prompts or visual images, or a combination of the two. The prompts may be emitted at a predetermined rate and may be synchronized. This invention is also directed to a method for administering care comprising, providing instructions to a rescuer. The instructions are either CPR instructions, ACLS instructions, or a combination of the two. Both the ACLS and CPR systems are capable of providing instructions for treating both adults and pediatric patients.

39 Claims, 20 Drawing Sheets

U.S. PATENT DOCUMENTS

| | | |
|---|---|---|
| 4,519,397 A | 5/1985 | Tabata |
| 4,588,383 A | 5/1986 | Parker et al. |
| 4,619,265 A | 10/1986 | Morgan |
| 5,088,037 A | 2/1992 | Battaglia |
| 5,239,988 A | 8/1993 | Swanson et al. |
| RE34,800 E | 11/1994 | Hutchins |
| 5,394,892 A | 3/1995 | Kenny et al. |
| 5,405,362 A | 4/1995 | Kramer et al. |
| 5,454,779 A | 10/1995 | Lurie et al. |
| 5,490,523 A | 2/1996 | Isaacson et al. |
| 5,575,284 A | 11/1996 | Athan et al. |
| 5,588,425 A | 12/1996 | Sackner et al. |
| 5,590,652 A | 1/1997 | Inai |
| 5,607,454 A | 3/1997 | Cameron et al. |
| 5,611,815 A | 3/1997 | Cole et al. |
| 5,631,552 A | 5/1997 | Ogawa et al. |
| 5,644,240 A | 7/1997 | Brugger |
| 5,645,522 A | 7/1997 | Lurie et al. |
| 5,662,106 A | 9/1997 | Swedlow et al. |
| 5,662,115 A | 9/1997 | Torp et al. |
| 5,662,690 A | 9/1997 | Cole et al. |
| 5,797,969 A | 8/1998 | Olson et al. |
| 5,868,794 A | 2/1999 | Barkley et al. |
| 5,913,685 A | 6/1999 | Hutchins |

OTHER PUBLICATIONS

Product Brochure from CPR Prompt® Rescue and Practice Aid, "CPR Refresher Book," County Line Ltd, LLC, 1996.

Cummins, et al., "Improving Survival from Sudden Cardiac Arrest: The 'Chain of Survival' Concept" *Circulation* 83:1832–1847 (1991).

Emergency Cardiac Care Committee, et al. "III. Adult Advanced Cardiac Life Support" *JAMA* 268:2172–2183 (1992).

EXTERNAL DEFIBRILLATOR WITH CPR PROMPTS AND ACLS PROMPTS AND METHODS OF USE

CONTINUING APPLICATION DATA

This application is a continuation in part of application Ser. No. 08/994,495, filed Dec. 19, 1997, now abandoned which is a continuation-in-part of application Ser. No. 08/965,347, filed Nov. 6, 1997 now abandoned.

FIELD OF THE INVENTION

This invention relates generally to a defibrillator with a built-in cardiopulmonary resuscitation ("CPR") prompt system. This invention also relates generally to a defibrillator with a built-in Advanced Cardiac Life Support ("ACLS") prompt system. Defibrillators include, manual defibrillators, automatic or semi-automatic external defibrillators (referred to collectively as "AEDs") and defibrillator trainers.

DESCRIPTION OF THE PRIOR ART

Each day thousands of Americans are victims of cardiac emergencies. Cardiac emergencies typically strike without warning, oftentimes striking people with no history of heart disease. Because of the potentially life threatening nature of cardiac emergencies, it is imperative that victims receive immediate care to prevent permanent damage to the brain or, worse yet, death. Cardiac emergencies include: acute myocardial infarction (commonly referred to as "heart attacks"); bradycardia; tachycardia; hypotension and pulmonary edema; ventricular fibrillation ("VF") and ventricular tachycardia ("VT"); pulseless electrical activity ("PEA"); and asystole. Each cardiac emergency has its own treatment protocol which is determined by the specific symptoms manifested by the victim.

One of the most common cardiac emergencies is sudden cardiac arrest ("SCA"). It is estimated that more than 1000 people per day are victims of sudden cardiac arrest in the United States alone.

SCA occurs when the heart stops pumping blood. Usually SCA is due to abnormal electrical activity in the heart, resulting in an abnormal rhythm (arrhythmia). One such abnormal rhythm, VF, is caused by abnormal and very fast electrical activity in the heart. During VF the heart cannot pump blood effectively. VF may be treated by applying an electric shock to the patient's heart through the use of a defibrillator. The shock clears the heart of the abnormal electrical activity (in a process called "defibrillation") by depolarizing a critical mass of myocardial cells to allow spontaneous organized myocardial depolarization to resume.

Another abnormal rhythm, treatable by defibrillation, is pulseless VT ("shockable VT"). Shockable VT consists of three consecutive QRS complexes originating from the ventricles and recurring at a rapid rate (over 100 beats/minute). More detailed information about electrocardiography and the various types of heart rhythms may be obtained from Wagner "Marriott's Practical Electrocardiography," 9th Ed. (1994).

It is important to note that not all abnormal heart rhythms are treatable by an electric shock. Several abnormal heart rhythms that are treated as a cardiac emergency require interventions other than defibrillation. However, it is possible for the nature of a cardiac emergency to change during the course of treatment. As a result a cardiac emergency initially having a heart rhythm that is not treatable by defibrillation may become a cardiac emergency where defibrillation is appropriate. Alternatively, a heart rhythm that is treatable by defibrillation may convert to a rhythm that is not treatable by defibrillation during the course of treatment. Accordingly, it is important to adapt the treatment protocol followed in administering care to a victim as the condition of the victim changes.

Even for the abnormal rhythms that are treatable by defibrillation, an electric shock does not always immediately restore a normal heart rhythm. Oftentimes, more than one shock is required.

Because blood may no longer be pumping effectively during a cardiac emergency, the chances of surviving decrease with time after the onset of the emergency. Brain damage can occur after the brain is deprived of oxygen for four to six minutes.

For SCA, if the initial defibrillation shocks are unsuccessful, CPR may be performed in order to keep oxygenated blood flowing to the brain. CPR may also be beneficial after a successful defibrillation shock when the post-shock heart rhythm does not pump a sufficient amount of blood. CPR can also prolong VF, thus maintaining a rhythm that can be analyzed and potentially defibrillated. Effective CPR may make the heart healthier for subsequent defibrillation in patients with VF.

Because quick response to a cardiac arrest is critically important, the American Heart Association ("AHA") developed the "Chain of Survival" guidelines, which recite the following steps:

1. Early access to an emergency medical service ("EMS"), such as by activating an emergency response system (e.g. calling an ambulance or calling "911");
2. Early CPR initiated by a bystander or other early caregiver to help the patient survive until more advanced care arrives;
3. Early defibrillation; and
4. Early application of Advanced Cardiac Life Support ("ACLS"), such as airway management, drugs, etc.

The benefits of this approach to survival are discussed in more detail in Cummins, et al. "Improving Survival from Sudden Cardiac Arrest: the 'Chain of Survival' Concept" *Circulation* 83:1832–1847 (1991). With the exception of the defibrillation step (#3.), these guidelines are appropriate for treating victims of all cardiac emergencies, not just SCA.

CPR is a combination of artificial respiration ("rescue breathing," of "expired air resuscitation") and artificial circulation ("external cardiac compression" or "external chest compression"). Typically, if the patient is unconscious and is not breathing, but has a pulse, rescue breathing only is required. Whereas, if the patient is unconscious, is not breathing, and has no pulse, rescue breathing along with external cardiac compression is required.

Rescue breathing is performed by first clearing and opening the air passage. Once the airway is cleared, if the patient is still unable to breathe, the rescuer pinches the nose of the patient and slowly breathes into the mouth of the patient until the patient's chest rises. Additionally, a barrier mask, bag-valve mask, automatic transport ventilators ("ATVs"), or oxygen-powered, manually triggered devices may be used by the rescuer during rescue breathing in order to protect the rescuer from direct contact with the patient's bodily fluids. According to current AHA guidelines, the patient should be ventilated by rescue breathing twice before performing the remaining steps of CPR. Once the patient has been ventilated twice, the patient's pulse is checked. If a pulse is present, and the patient's breathing has not resumed on its own, then the rescue breathing procedure should be continued.

Typically with VF, the patient is unconscious, is not breathing and has no pulse. As a result, the patient requires rescue breathing combined with external chest compression.

The rate at which CPR is administered to a patient also depends upon the age of the patient. For example, under the AHA protocol, CPR is performed by administering a repeated sequence of fifteen compressions to two inflations for an initial period of one minute for an adult patient. The pulse and breathing are checked after each one minute interval. Up-to-date CPR protocols recommended by the AHA may be obtained from the AHA internet web site at www.amhrt.org.

The current standards recommended by the AHA for CPR are:

Make sure the scene is safe for help.

Make sure you have the universal precautions: gloves, pocket mask, etc.

Make sure you know how many patients you have.

Determine if they are conscious by tapping and shouting "Are you okay?"

If there is no response, have someone call 911.

Position the patient on their back.

Open the airway with a head-tilt, chin-lift or jaw-thrust maneuver.

Look-listen-and-feel for breaths. Check breathing for 5–10 seconds.

If they are not breathing, ventilate twice.

Check pulse for 10 seconds.

If there is no pulse, begin chest compressions and breathing at the following rate for one minute (depending upon the age of the patient):

| Age of Patient | Compressions | Breaths |
| --- | --- | --- |
| Infant (0–1 yr) | 5 | 1 |
| Child (1–8 yrs) | 5 | 1 |
| Adult (8+ yrs) | 15 | 2 |

After one minute, recheck the pulse and repeat the compression/breathing cycle rechecking the pulse at one minute intervals. If there is more than one rescuer, one rescuer should perform the chest compressions and then pause while the other rescuer performs the rescue breathing. Attending to the airway, breathing and circulation, as described above is referred to as "ABCs" of CPR.

Because of the importance of early CPR in the "Chain of Survival", the AHA and the American Red Cross have promoted training potential rescuers in the basics of CPR for use in medical emergencies for many years. In addition to use in cardiac emergencies, basic CPR is also important in treating patients of a stroke, drowning, auto accidents, suffocation, electrocution, and drug intoxication resulting in cardiac arrest. Although many people have gone through CPR training, most have not maintained their skills, which are quickly forgotten when unused. Even for professionals, it can be difficult to remember protocol changes to a procedure during a given emergency; this is particularly true as the procedures become more complex and as standards change. For some first responders, such as police officers or flight attendants, it can be even more difficult to remember protocol changes because administering CPR or attending to a cardiac emergency is not their primary occupation.

Over the years, many tools have been developed to assist emergency personnel in delivering CPR and recalling the correct sequence of the various steps involved in administering CPR. For example, Parker et al. (U.S. Pat. No. 4,588,383) provides a voice prompting system for a rescuer to follow during a rescue operation. This system is an interactive synthetic speech CPR trainer and prompter. The system has several actuator push buttons for the user to select so that the correct instructions are provided. By providing step-by-step prompting in the protocols and procedures of CPR, this device can guide a rescuer through a CPR protocol.

Another system, developed by Battaglia, is a portable rescue administration aid device (U.S. Pat. No. 5,088,037). This device is designed to be worn on the wrist of a rescuer to assist the rescuer in carrying out the rescue operation. The device provides instructions that can be easily modified and updated, as needed. Additionally, the device can be coupled with other electronic medical storage means for retrieving medical data. The device provides a push-button front-end, into which the rescuer can enter information such as age of the patient, whether the patient is unconscious, whether breathing is present, etc. This device also features an internal timer that is activated when the device is turned-on. Battaglia produces four tones to highlight the steps of the rescue procedure. A recall function is provided that allows the user to reverse the sequence so that the user can recall any message in the instruction sequence and proceed forward from that point.

Swanson et al. (U.S. Pat. No. 5,239,988) developed a CPR aid in the form of a wrist watch. The Swanson device emits audible signals at a rate corresponding to the number of compressions per minute selected. Alternatively, the watch provides a visual signal for timing CPR in noisy areas. Additionally, pulmonary inflation is indicated at appropriate intervals depending upon which compression rate is chosen initially.

Hutchins (U.S. Pat. No. 4,583,524, now Reissue Re. 34,800) developed a self-powered electronic CPR prompting system. The Hutchins system provides a portable device that provides prompts to those previously trained in CPR. Hutchins provides multiple input buttons for the user to enter information regarding the age of the patient, the number of rescuers involved and whether the patient is choking or unconscious. Hutchins enables the user to interactively change the CPR prompts during the course of treatment if the condition of the patient changes.

One drawback of these systems is that they require the rescuer to carry a separate piece of equipment to the emergency setting. This may not always be feasible, depending on the nature of the rescue.

Following the administration of CPR, the availability of ACLS is critical to the victim's survival, particularly if CPR alone does not resuscitate the victim. ACLS includes, determining the blood pressure of the victim, determining the blood volume of the victim, identifying the type of arrhythmia present and providing treatment which is directed to the specific physiological condition, including defibrillation, administration of drugs, intubation, administering fluids, administering oxygen, and continuing CPR.

Kramer et al. (U.S. Pat. No. 5,405,362) describes an interactive external defibrillator and drug injection system that makes recommendations to the operator for treatment of a patient, based on the input data received. The device described by Kramer et al. also provides a means for vascular drug delivery by intraosseous ("IO") injection.

In addition to widespread training on CPR over the years, there has also been an increase in the number of people who are trained in the proper use of an external defibrillator. The increased number of users increases the likelihood that a trained defibrillator user will be available during an emergency and thus could ultimately reduce the defibrillator deployment time. As the number of people trained in CPR and defibrillator usage increases, however, the frequency with which each rescuer uses the skills developed during training decreases. Depending upon the amount of time since the defibrillator was last used or CPR last performed, the rescuer may be slow to respond as he or she tries to recall all the steps involved in properly deploying a defibrillator and performing CPR. In addition to the protocol for performing CPR, the use of a defibrillator in conjunction with CPR has a separate, albeit related, protocol that must be recalled during an emergency. Such a protocol review, while necessary, delays the speed with which defibrillation and CPR can be performed on the patient. With every second that passes, the likelihood of a patient surviving neurologically intact decreases.

These protocols are further complicated by the need to delivery ACLS for cardiac emergencies that are not treatable by defibrillation. It is also important for an emergency care giver to appreciate that the nature of the emergency can change during treatment which can result in a change in the treatment protocol.

For example, according to the current AHA guidelines, if defibrillation is unsuccessful in converting the heart rhythm after the administration of three consecutive shocks, CPR should be performed for a period of one minute. This "defibrillation—CPR" protocol should be repeated until the patient can be transported to an appropriate medical care facility while a victim has a heart rhythm that is treatable by defibrillation. More detailed information about the "defibrillation—CPR" protocol, including information relating to ACLS, is available in Emergency Cardiac Care Committee, et al., "III. Adult Advanced Cardiac Life Support" *JAMA* 268:2172–2183 (1992). This information may be updated from time to time.

In response to the AHA's 'Chain of Survival', defibrillator manufacturers have spent many years improving defibrillator technology. The smallest automatic external defibrillator ("AED") developed to date is the Heartstream, Inc. FORERUNNER® AED. Once deployed, this small, lightweight AED is capable of analyzing a patient's electrocardiogram ("ECG") to determine whether the heart rhythm can be treated with an electric shock. Once the AED determines that a shock is appropriate, it notifies the rescuer that a shock is advised and instructs the rescuer to deliver a shock by pressing the appropriate button. More detailed information directed to AEDs can be found in Cameron et al. U.S. Pat. No. 5,607,454 and Cole et al. U.S. Pat. No. 5,611,815. The FORERUNNER® prompts the user to deploy the defibrillator by instructing the user to, for example, "attach pads."

An additional feature of the FORERUNNER® AED is that a "pause period" can be programmed into the device so that after a predetermined number of shocks the AED ceases analyzing the patient's heart rhythm in order to allow the user to administer CPR. The pause period lasts for a pre-programmed period of time. Once the pause period has ended, the AED then begins analyzing the heart rhythm to determine whether or not a shock is necessary. The FORERUNNER® AED also has a voice prompt that says "if necessary, begin CPR," if the patient is not in a shockable rhythm. A pause period can also be programmed after a "no shock advised" decision.

Another AED, the LifePak 100 developed by Physio-Control Corp., prompts the user to, for example, "perform CPR, deliver 2 breaths and 15 chest compressions." These prompts are displayed on an enunciator panel.

Other patient monitoring equipment, such as pulse oximeters (see, e.g. U.S. Pat. Nos. 5,490,523; 5,590,652; 5,588,425; and 5,575,284), pulse detectors (see e.g. U.S. Pat. Nos. 4,519,397; and 4,181,134), blood pressure detectors, or hemodynamic monitors (see, e.g. U.S. Pat. Nos. 5,644,240; and 5,631,552), are known in the art and are not described herein.

Many other defibrillators, including manual defibrillators, and defibrillator trainers have been developed and are known in the art, although not discussed herein.

The disclosures of the patients cited herein are incorporated by reference.

What is needed is a defibrillator or defibrillator trainer that can also instruct a rescuer in the proper protocol for delivering CPR and ACLS to an adult or child victim. Further, what is needed is a defibrillator or defibrillator trainer that can dynamically alter the instructions provided to the rescuer based on changes in the patient's condition or the level of skill of the operator. Such a device allows the rescuer to treat the patient based on recommendation from the defibrillator using a combination of signs and symptoms as well as heart rate and heart rhythm information, and not treat the device. Finally, what is needed is a defibrillator that allows the rescuer to begin CPR prompts on command.

SUMMARY OF THE INVENTION

This invention is directed to a defibrillator system having a defibrillator with an energy source, an electrode interface and an audible sound generator, wherein the electrode interface is in electrical communication with the energy source. The defibrillator may be a manual defibrillator, an AED, or a defibrillator trainer. The defibrillator system also has an instruction generator which communicates with the audible sound generator. The defibrillator system can also have a visual image generator which also communicates with the instruction generator. The instruction generator generates audible prompts or visual images, or a combination of the two. The prompts can be emitted at a predetermined rate or can be synchronized.

This invention is also directed to a defibrillator system having a defibrillator with an energy source, an electrode interface and a visual image generator, wherein the electrode interface is in electrical communication with the energy source. The defibrillator system also has an instruction generator which communicates with the visual image generator. The defibrillator system can also have an audible sound generator which also communicates with the instruction generator. The instruction generator generates audible prompts or visual images, or a combination of the two. The prompts can be emitted at a predetermined rate or can be synchronized.

This invention is also directed to a defibrillator capable of generating audible sound, wherein the defibrillator instructs a rescuer on performing CPR or ACLS. The defibrillator is also capable of generating visual images. The instructions are audible prompts or visual images, or a combination of the two. The prompts can be emitted at a predetermined rate or can be synchronized.

This invention is also directed to a defibrillator capable of generating visual images, wherein the defibrillator instructs a rescuer on performing CPR or ACLS. The defibrillator is also capable of generating audible sound. The instructions can be audible prompts or visual images, or a combination of the two. The prompts can be emitted at a predetermined rate and can be synchronized.

This invention is also directed to a method for administering care which comprises providing CPR or ACLS instructions to a rescuer. The instructions include providing prompts for delivering chest compressions, for delivering artificial breathing, for delivering drugs, for administering oxygen, for intubating, and other instructions for delivering ACLS. The instructions are visual prompts, audible prompts or a combination of the two. The prompts are emitted at a predetermined rate and can be synchronized.

DESCRIPTION OF THE PREFERRED EMBODIMENTS

Figure 1:
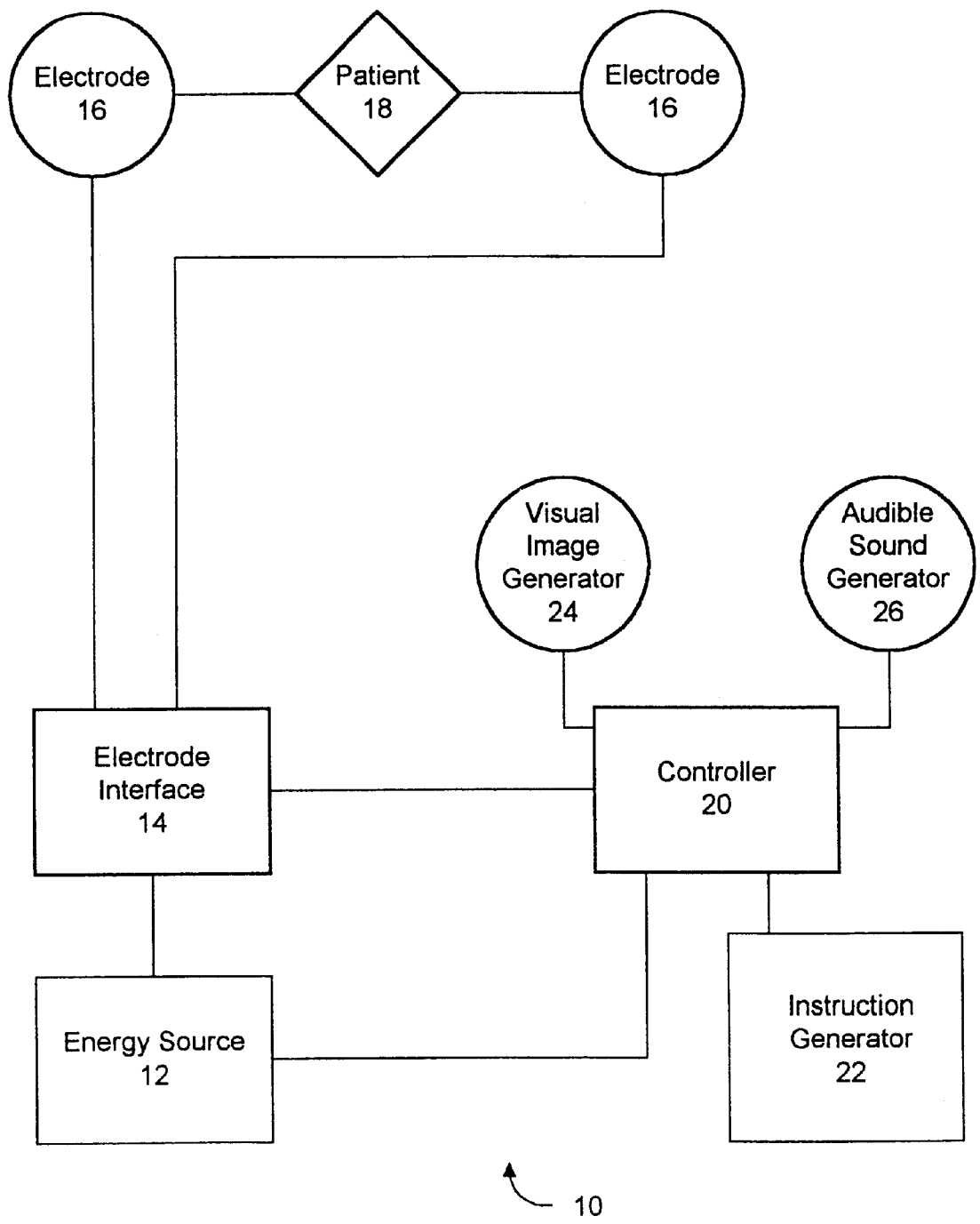
FIG. 1 is a diagrammatic representation of a defibrillator system.

FIG. 1 is a schematic block diagram of a defibrillator system 10 according to a preferred embodiment of this invention. The defibrillator system 10 comprises an energy source 12 to provide voltage or current pulses. A controller 20 operates an electrode interface 14 to selectively connect and disconnect energy source 12 to and from a pair of electrodes 16 electrically attached to a patient 18 to provide electrotherapy to the patient. The defibrillator system 10 may be a manual defibrillator, an AED, or a defibrillator trainer that simulates the behavior of a manual defibrillator or AED in use.

In addition, controller 20 performs a protocol using information from an instruction generator 22 to provide instructions to the defibrillator operator. The instruction generator 22 may also activate protocol changes being performed by the defibrillator 10 based on information received from the controller 20. For example, controller 20 may assess the nature of the rhythm detected, the amount of time that has passed or the number of consecutive, or total, shocks that have been delivered, or other information that may be provided (either physiological information monitored directly from the victim, or interactive data relating to the victim's condition as provided by the rescuer) in determining which protocol to follow. Additionally, the controller 20 may be operating based on a combination of stored or generated data and interactive data, which would be the case if the defibrillator was either a trainer or was being used in training mode. The amount or level of instructions generated by the instruction generator 22 can be modified according to the particular needs of the end user or the protocol followed by the organization controlling the operation of the defibrillator. For example, prompts may be limited to delivering defibrillation shocks and administering CPR, or may be expanded to include identification of additional arrhythmias and administration of ACLS care.

The instructions may be delivered via a visual image generator 24, such as by displaying, among other things, commands to the rescuer (either written or graphic representations). The visual image generator 24 may be, for example, a liquid crystal display ("LCD"). Additionally, an audible sound generator 26 may be provided that broadcasts audible commands from the instruction generator 22. Audible commands may include verbal commands directing the rescuer in the proper sequence and timing for administering CPR or ACLS, or audible timing tones, such as those generated by a metronome, for timing the administration of CPR or ACLS. Activation of the visual image generator 24 and the audible sound generator 26 is controlled by the controller 20 in response to the information received from the instruction generator 22. Instruction generator 22 may be a set of software commands performed by controller 20.

Additionally, existing buttons (not shown) may be used to enter information regarding the age of the patient, number of patients, number of rescuers, or any other information that may be required to determine the correct protocol to follow in delivering CPR or ACLS.

Figure 2:
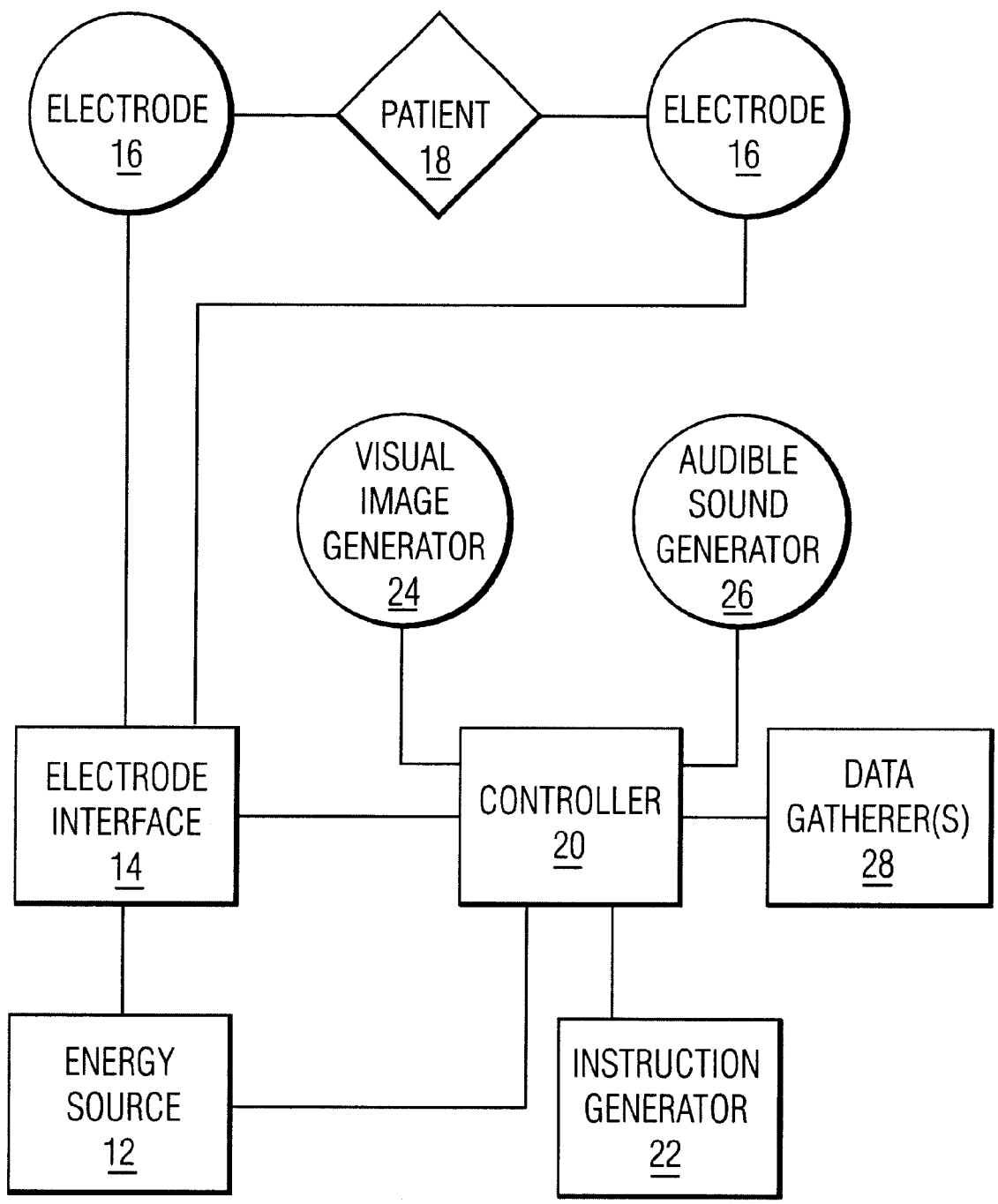
FIG. 2 is a diagrammatic representation of a defibrillator system according to an alternate embodiment which provides data gatherer(s).

As shown in FIG. 2, the defibrillator system 10 may also have one or more data gatherers 28 capable of gathering additional data from the patient. For example, the defibrillator may also have associated with it a pulse oximeter, a pulse detector, a blood pressure detector or a hemodynamic monitor. The defibrillator may have any one of the data gatherers, a combination of the data gatherers, or all of the data gatherers providing data to the controller 20. These additional data gathering devices may be integral with the defibrillator system 10 or may be auxiliary equipment capable of communicating data to the defibrillator system 10. Communication between the additional data gatherers 28 may be accomplished by any method known in the art. For example, data may be communicated via a cable linked between the defibrillator and the auxiliary data gatherer. Alternatively, data may be communicated by using light wave transmission (for example, IR, or other suitable light waves), radio wave transmission, audio wave transmission, or magnetic wave transmission. Another possible means of transmitting data would be by providing the data gatherer with a voice generator, the speech patterns would then be interpreted by the defibrillator using voice recognition software. Alternatively, the user could read the displayed result from the data gatherer 28 and the defibrillator could use voice recognition software to incorporate the results into a treatment algorithm.

Figure 3:
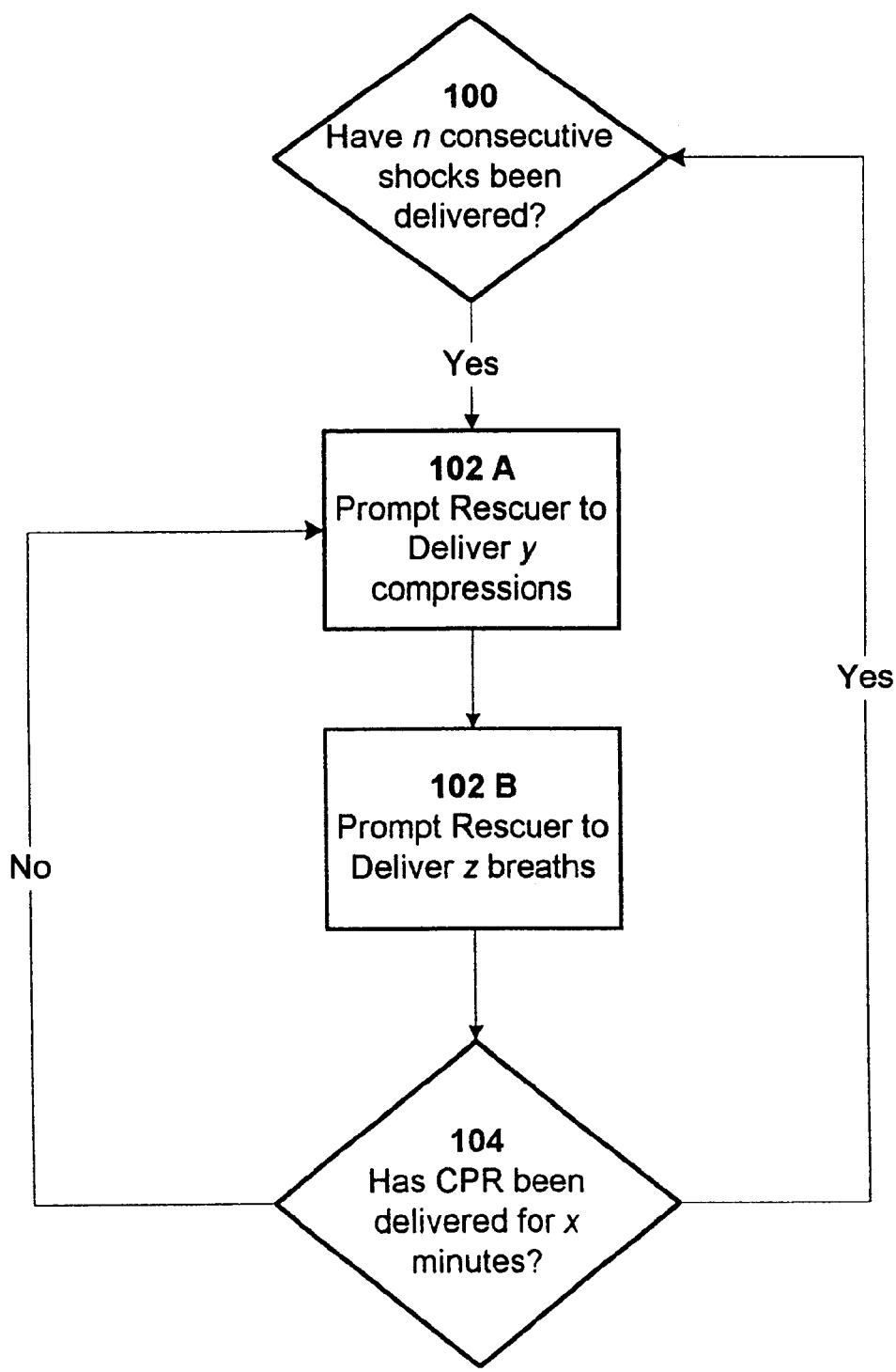
FIG. 3 is a flow chart demonstrating a defibrillator operating to deliver CPR prompts according to a method of this invention wherein instructions are provided for a set period of time.

FIG. 3 is an example of a defibrillator operation method according to this invention. The defibrillator 10 determines the number of consecutive shocks that have been delivered 100. Once n consecutive shocks have been delivered, the defibrillator 10 instructs the rescuer in the protocol for administering CPR (the "CPR prompt mode" or "CPR instruct mode") 102.

During the CPR instruct mode 102, the defibrillator 10 instructs the rescuer to deliver y compressions 102 A, where y is a number preprogrammed into the defibrillator 10. For example, y could be the number of compressions required under the AHA protocol for an adult or the number of compressions required by the protocol of a specific jurisdiction. Once the defibrillator has instructed the rescuer to deliver y compressions 102 A, the defibrillator 10 instructs the rescuer to delivery z breaths 102 B. For example, z could be the number of breaths required under the AHA protocol for an adult. The sequence of delivering y compressions and z breaths is repeated until x minutes have passed 104, where x is the amount of time of the CPR instruct mode in the protocol that the device has been programmed to follow.

Variations in the CPR protocol, including the addition of prompting steps, is within the scope of this invention. More specific examples of possible embodiments of the prompting steps are discussed in more detail below.

Once CPR has been delivered for the programmed amount of time 104, the defibrillator 10 returns to counting the number of consecutive shocks administered 100.

Figure 4:
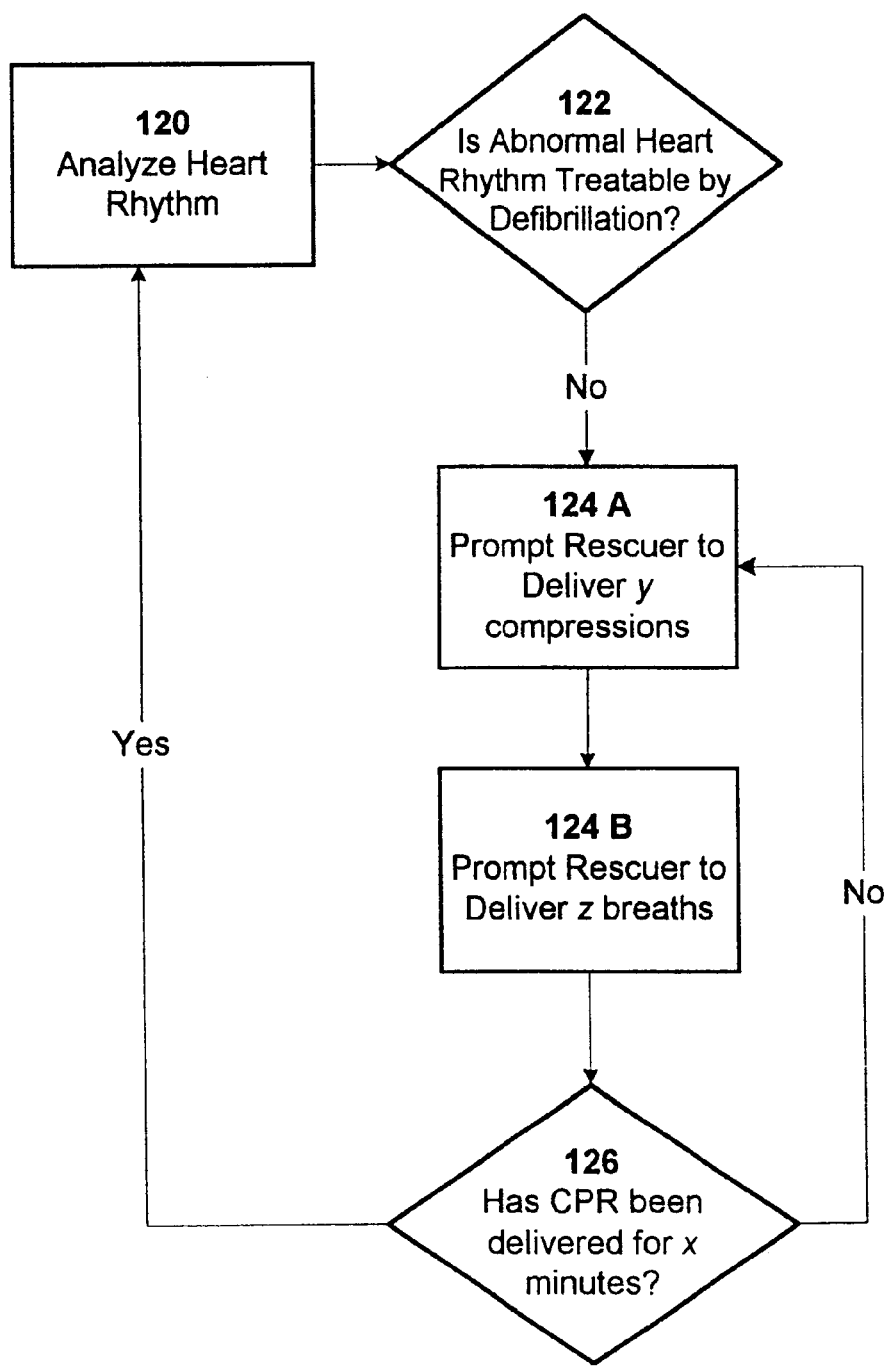
FIG. 4 is a flow chart demonstrating a defibrillator operating to deliver CPR prompts according to an alternative method of this invention wherein instructions are provided for a set period of time. The step of analyzing the heart rhythm is included.

FIG. 4 is another example of a defibrillator operation method according to this invention. The defibrillator analyzes the heart rhythm 120 and determines whether the heart rhythm is shockable (i.e., is treatable by the administration of a defibrillating shock) 122. The heart rate analyzed by the defibrillator may be real-time data from an actual patient receiving treatment, or may be simulated or historical data used for purposes of training. If the heart rhythm is abnormal but is not treatable by defibrillation, the defibrillator 10 instructs the rescuer in the correct protocol for administering CPR.

During the CPR instruct mode, the defibrillator 10 instructs the rescuer to deliver y compressions 124 A, where y is a number preprogrammed into the defibrillator 10. For example, y could be the number of compressions required under the AHA protocol for an adult. Once the defibrillator has instructed the rescuer to deliver y compressions 124 A, the defibrillator 10 instructs the rescuer to deliver z breaths 124 B. For example, z could be the number of breaths required under the AHA protocol for an adult. The sequence of delivering y compressions and z breaths is repeated until x minutes have passed 126, where x is the amount of time of the CPR instruct mode in the protocol that the device has been programmed to follow.

Additional prompting steps or other variations in this protocol are within the scope of the invention. More specific examples of possible embodiments of the prompting steps are discussed in more detail below.

In a preferred embodiment of the invention shown in FIGS. 1 and 4, the invention is implemented by modifying the software of the FORERUNNER® defibrillator to include the CPR prompts. Other defibrillators, such as manual defibrillators, or defibrillator trainers could be modified to include the CPR prompts as well.

Following the CPR instruct mode 124, the defibrillator 10 again analyzes the heart rhythm of the patient to determine whether or not the rhythm is shockable. If the defibrillator detects a normal heart rhythm, the defibrillator 10 continues to analyze the patient's heart rhythm until such time as an abnormal rhythm is again detected. Once the abnormal rhythm is detected, the defibrillator determines whether the rhythm is shockable 122. If the rhythm is not shockable, the CPR prompting steps 124 are repeated.

Figure 5:
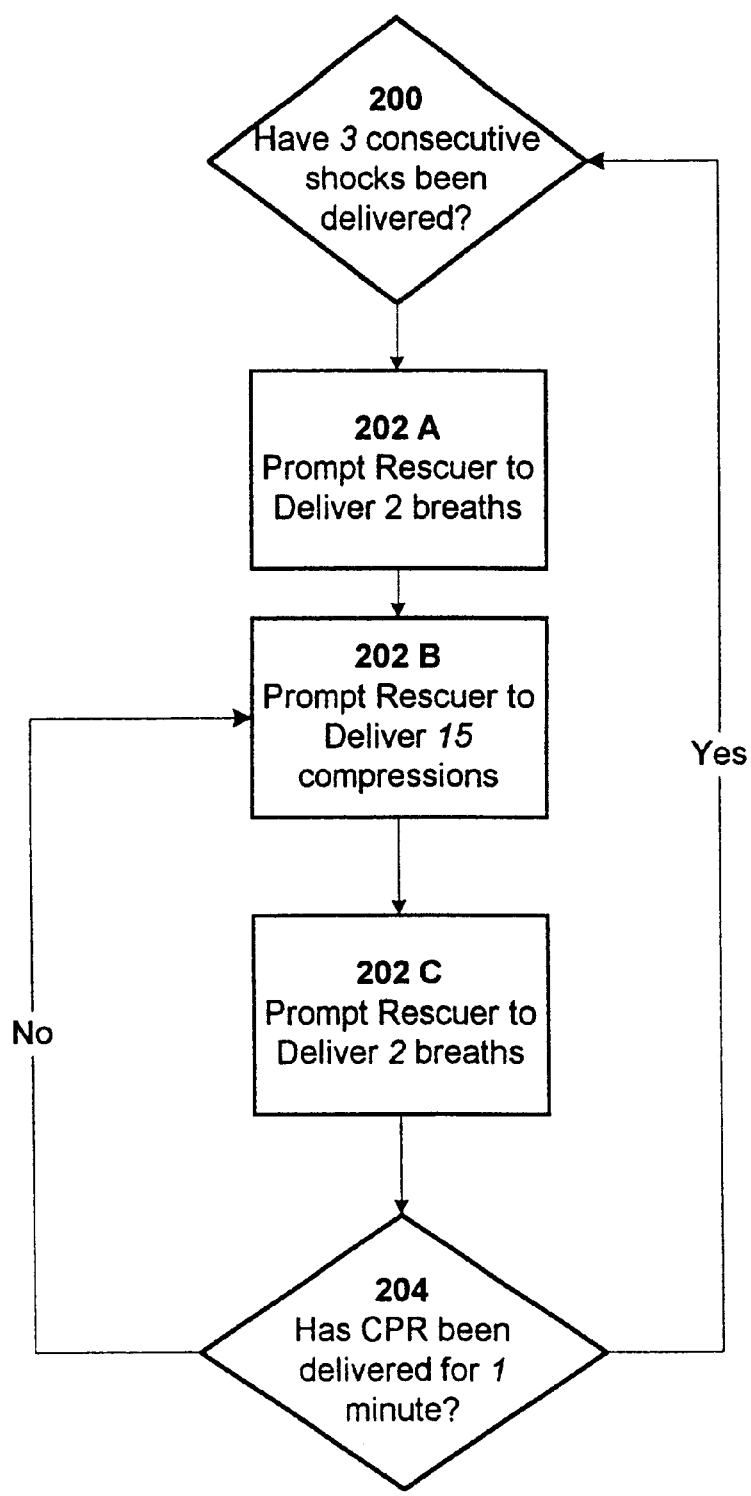
FIG. 5 is a flow chart demonstrating a defibrillator operating to deliver CPR prompts for a set period of time according to the AHA protocol for administering CPR to an adult.

FIG. 5 is yet another example of a defibrillator operation method according to this invention. The defibrillator 10, programmed to follow the AHA protocol for an adult patient, determines whether 3 consecutive shocks have been delivered 200. Once 3 shocks have been delivered, the defibrillator 10 instructs the rescuer in the correct protocol for administering CPR (the "CPR prompt mode" of "CPR instruct mode") 202.

During the CPR instruct mode 202, the defibrillator 10 instructs the rescuer to deliver 2 breaths 202 A. Then, the defibrillator 10 instructs the rescuer to deliver 15 compressions 202 B. Once the defibrillator has instructed the rescuer to deliver 15 compressions 202 B, the defibrillator 10 instructs the rescuer to deliver 2 breaths 202 C. The sequence of delivering 15 compressions 202 B and 2 breaths 202 C is repeated until 1 minute has passed 204.

As discussed above, additional prompting steps or other variations in this protocol are within the scope of the invention. More specific examples of possible embodiments of the prompting steps are discussed in more detail below.

Following the CPR instruct mode 202, the defibrillator 10 returns to counting the number of consecutive shocks administered 200.

Figure 6:
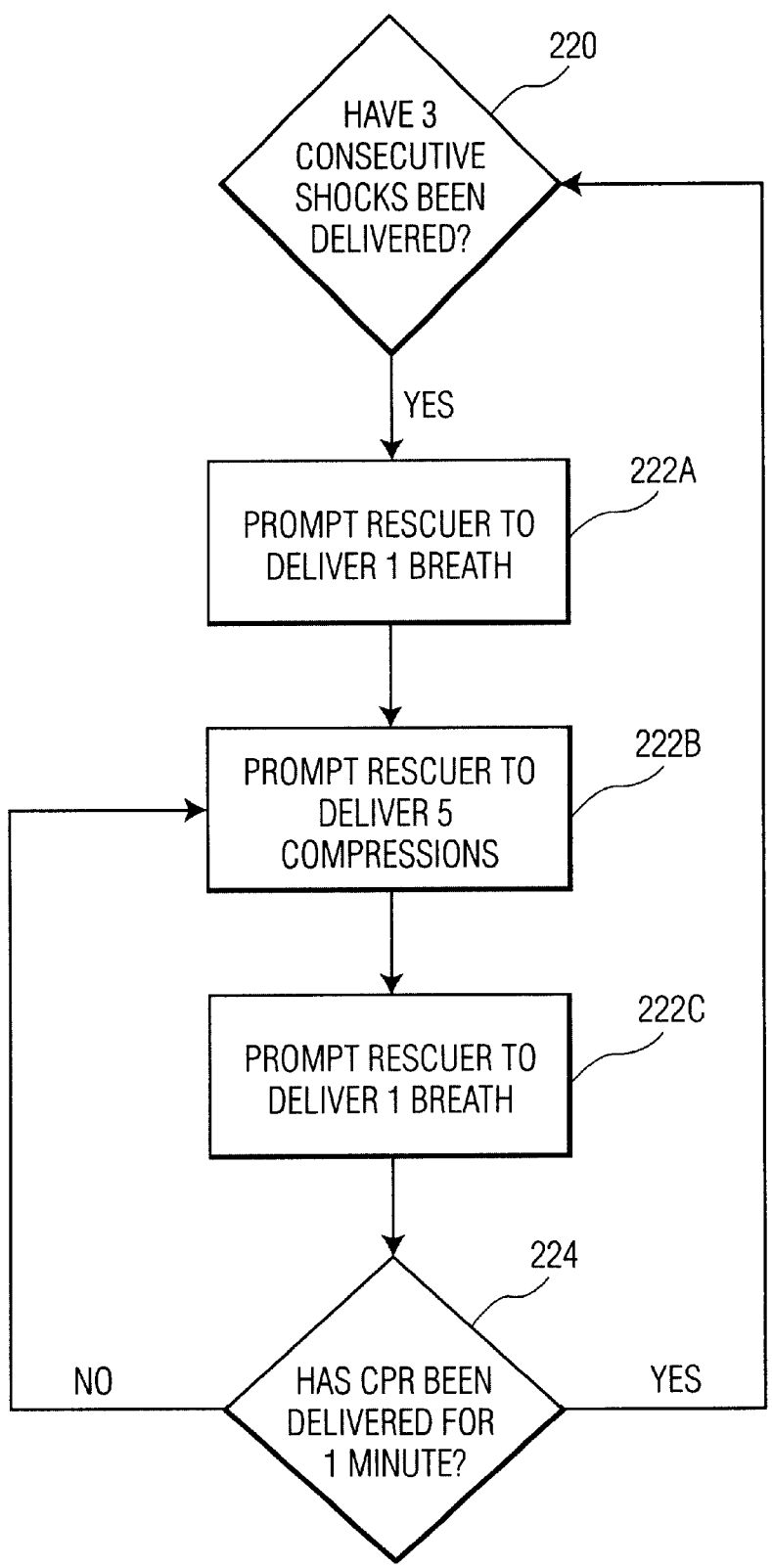
FIG. 6 is a flow chart demonstrating a defibrillator operating to deliver CPR prompts for a set period of time according to the AHA protocol for administering CPR to an infant or child.

In the example shown in FIG. 6, the defibrillator 10, programmed to follow the AHA protocol for treating an infant or child patient, determines whether 3 consecutive shocks have been delivered 220. Once 3 shocks have been delivered, the defibrillator 10 instructs the rescuer in the correct protocol for administering CPR (The "CPR prompt mode" of "CPR instruct mode") 222.

During the CPR instruct mode 222, the defibrillator 10 instructs the rescuer to deliver 1 breath 222 A. Then, the defibrillator 10 instructs the rescuer to deliver 5 compressions 222 B. Once the defibrillator has instructed the rescuer to deliver 5 compressions 222 B, the defibrillator 10 instructs the rescuer to deliver 1 breath 222 C. The sequence of delivering 5 compressions 222 B and 1 breath 222 C is repeated until 1 minute has passed 224.

Additional prompting steps or other variations in this protocol are within the scope of the invention. Examples of possible embodiments of the prompting steps are discussed in more detail below.

Following the CPR instruct mode 222, the defibrillator 10 returns to counting the number of consecutive shocks administered 220.

Figure 7:
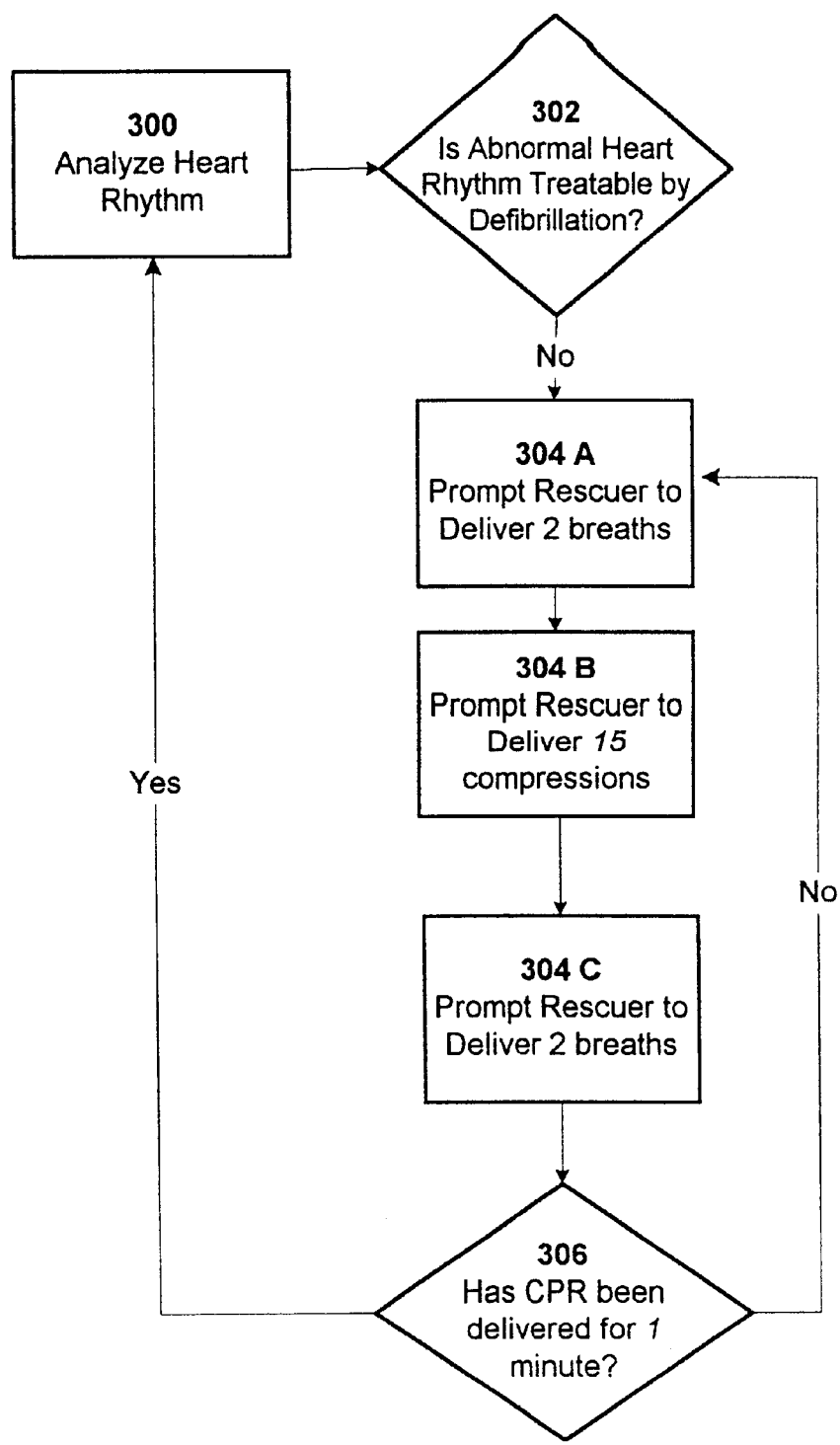
FIG. 7 is a flow chart demonstrating a defibrillator operating to deliver CPR prompts for a set period of time according to the AHA protocol for administering CPR to an adult. The step of analyzing the heart rhythm is included.

In the example shown in FIG. 7, the defibrillator 10, programmed to follow the AHA protocol for treating an adult, analyzes the heart rhythm 300 and determines whether the heart rhythm is shockable (i.e., is treatable by the administration of a defibrillating shock) 302. The heart rate analyzed by the defibrillator may be real-time data from an actual patient receiving treatment, or may be simulated or historical data used for purposes of training. If the heart rhythm is abnormal and is not treatable by defibrillation, the defibrillator 10 instructs the rescuer in the correct protocol for administering CPR.

During the CPR instruct mode, the defibrillator 10 instructs the rescuer to deliver 2 breaths 304 A. Then, the defibrillator 10 instructs the rescuer to deliver 15 compressions 304 B. Once the defibrillator has instructed the rescuer to deliver 15 compressions 304 B, the defibrillator 10 instructs the rescuer to deliver 2 breaths 304 C. The sequence of delivering 15 compressions 304 B and 2 breaths 304 C may be repeated until 1 minute has passed 306.

Additional prompting steps or other variations in this protocol are within the scope of the invention. Examples of possible embodiments of the prompting steps are discussed in more detail below.

Following the CPR instruct mode 304, the defibrillator 10 again analyzes the heart rhythm of the patient to determine whether or not the rhythm is shockable. If the defibrillator detects a normal heart rhythm, the defibrillator 10 continues to analyze the patient's heart rhythm until such a time as an abnormal rhythm is again detected. Once the abnormal rhythm is detected, the defibrillator determines whether the rhythm is shockable 302.

Figure 8:
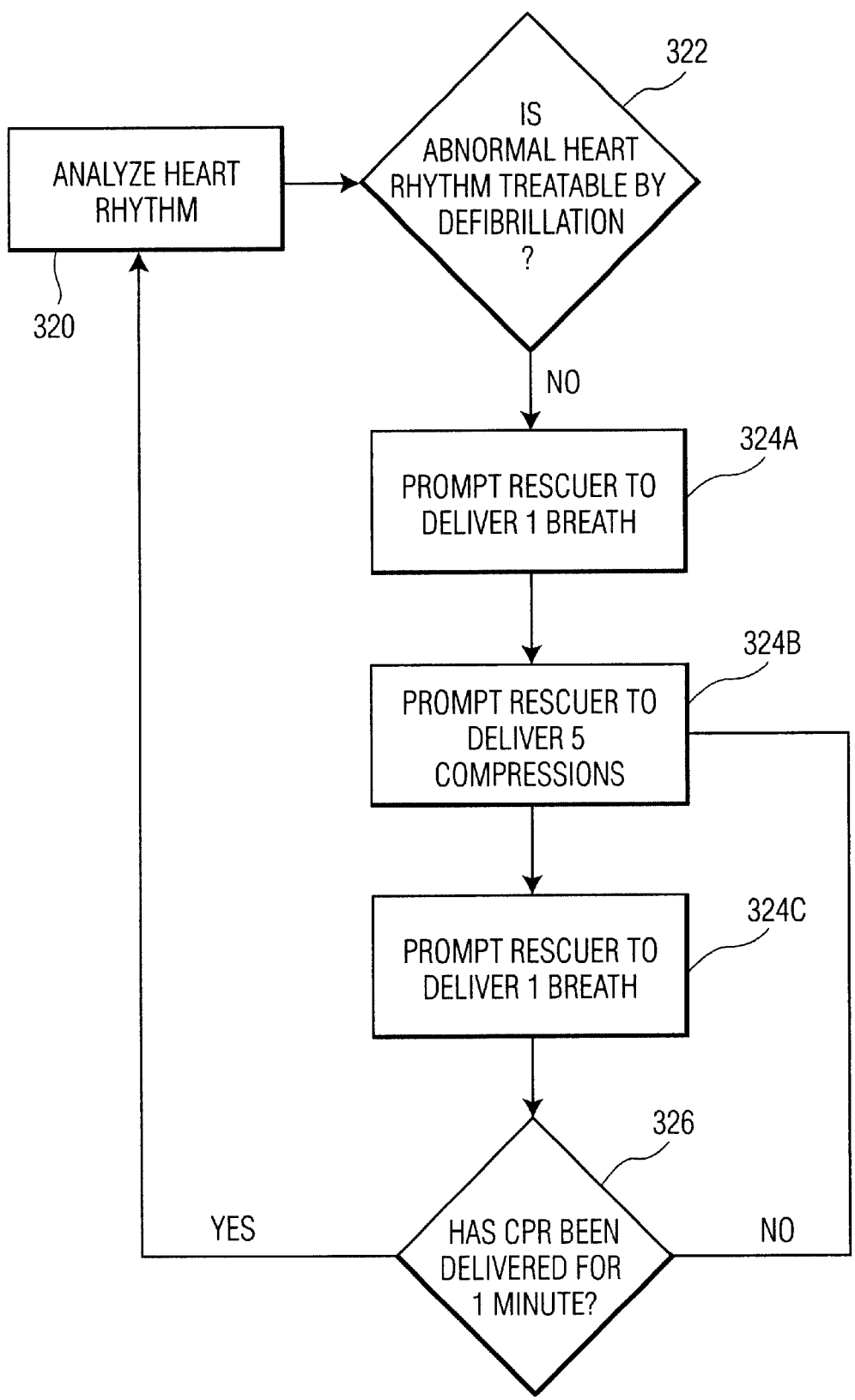
FIG. 8 is a flow chart demonstrating a defibrillator operating to deliver CPR prompts for a set period of time according to the AHA protocol for administering CPR to an infant or child. The step of analyzing the heart rhythm is included.

In the example shown in FIG. 8, the defibrillator 10, programmed to follow the AHA protocol for treating an infant or child, analyzes the heart rhythm 320 and determines whether the heart rhythm is shockable (i.e., is treatable by the administration of a defibrillating shock) 322. The heart rate analyzed by the defibrillator may be real-time data from an actual patient receiving treatment, or may be simulated or historical data used for purposes of training. If the heart rhythm is abnormal but not treatable by defibrillation, the defibrillator 10 instructs the rescuer in the correct protocol for administering CPR.

During the CPR instruct mode 324, the defibrillator 10 instructs the rescuer to deliver 1 breath 324 A. Then, the defibrillator 10 instructs the rescuer to delivery 5 compressions 324 B. Once the defibrillator has instructed the rescuer to deliver 5 compressions 324 B, the defibrillator 10 instructs the rescuer to delivery 1 breath 324 C. The sequence of delivering 5 compressions 324 B and 1 breath 324 C may be repeated until 1 minute has passed 326.

Additional prompting steps or other variations in this protocol are within the scope of the invention. Examples of possible embodiments of the prompting steps are discussed in more detail below.

Following the CPR instruct mode 324, the defibrillator 10 again analyzes the heart rhythm of the patient to determine whether or not the rhythm is shockable. If the defibrillator detects a normal heart rhythm, the defibrillator 10 continues to analyze the patient's heart rhythm until such time as an abnormal rhythm is again detected. Once the abnormal rhythm is detected, the defibrillator determines whether the rhythm is shockable 322.

Figure 9:
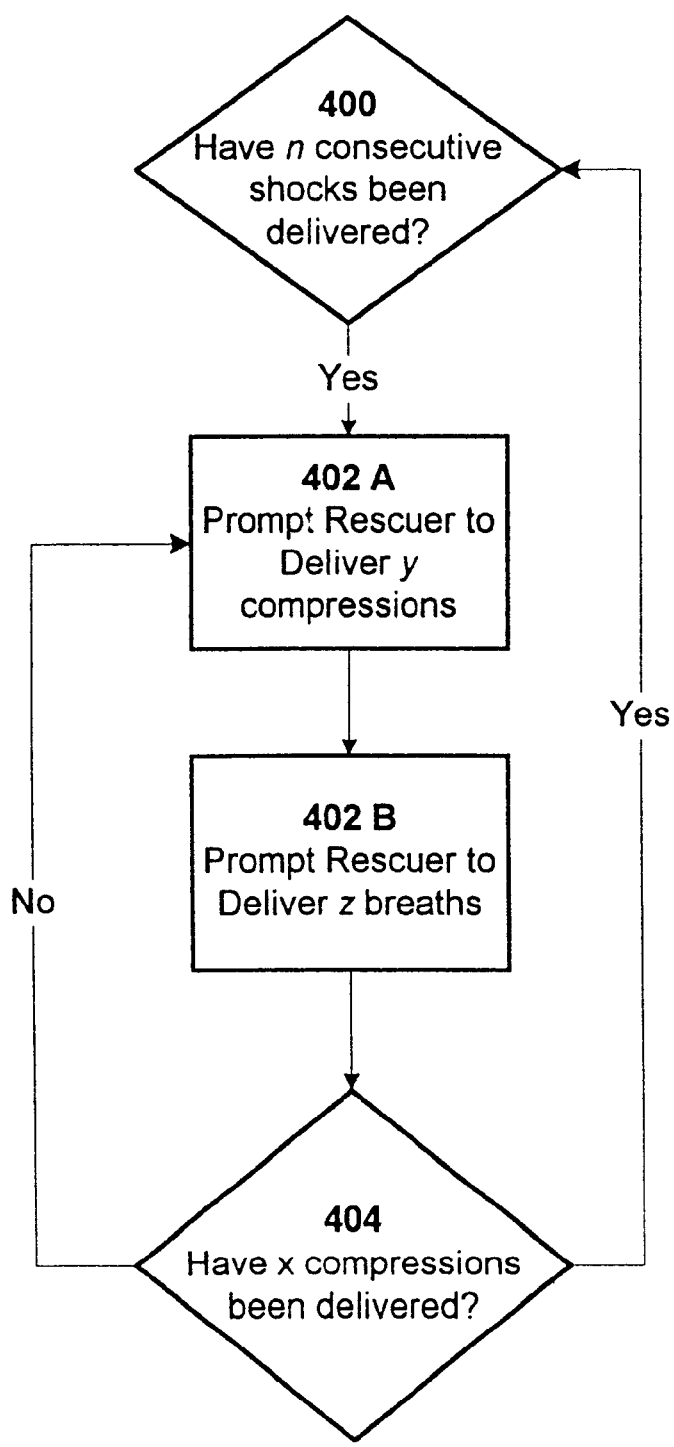
FIG. 9 is a flow chart demonstrating a defibrillator operating to deliver CPR prompts for a set number of compressions according to an alternative method of this invention.

FIG. 9 is an example of a defibrillator operation method according to this invention. The defibrillator 10 determines the number of consecutive shocks that have been delivered 400. Once n consecutive shocks have been delivered, the defibrillator 10 instructs the rescuer in the protocol for administering CPR (the "CPR prompt mode" or "CPR instruct mode") 402.

During the CPR instruct mode 402, the defibrillator 10 instructs the rescuer to deliver y compressions 402 A, where y is a number preprogrammed into the defibrillator 10. For example, y could be the number of compressions required under the AHA protocol for an adult or the number of compressions required by the protocol of a specific jurisdiction. Once the defibrillator has instructed the rescuer to deliver y compressions 402 A, the defibrillator 10 instructs the rescuer to deliver z breaths 402 B. For example, a protocol could be programmed where y is 10 and z is 2 (10 compressions to 2 breaths) and x is 50, thus requiring the steps of 402 A and 402 B to be repeated until a total of 50 compressions had been delivered during a CPR prompting period.

In another example, a protocol could be programmed where y is 5 and z is 1 (5 compressions to 1 breath) and x is 25, thus requiring the steps of 402 A and 402 B to be repeated until a total of 25 compressions had been delivered during that particular CPR prompting period.

Variations in the CPR protocol, including the addition of prompting steps, is within the scope of this invention. More specific examples of possible embodiments of the prompting steps are discussed in more detail below.

Once CPR has been delivered for the programmed number of compressions 404, the defibrillator 10 returns to counting the number of consecutive shocks administered 400.

Figure 10:
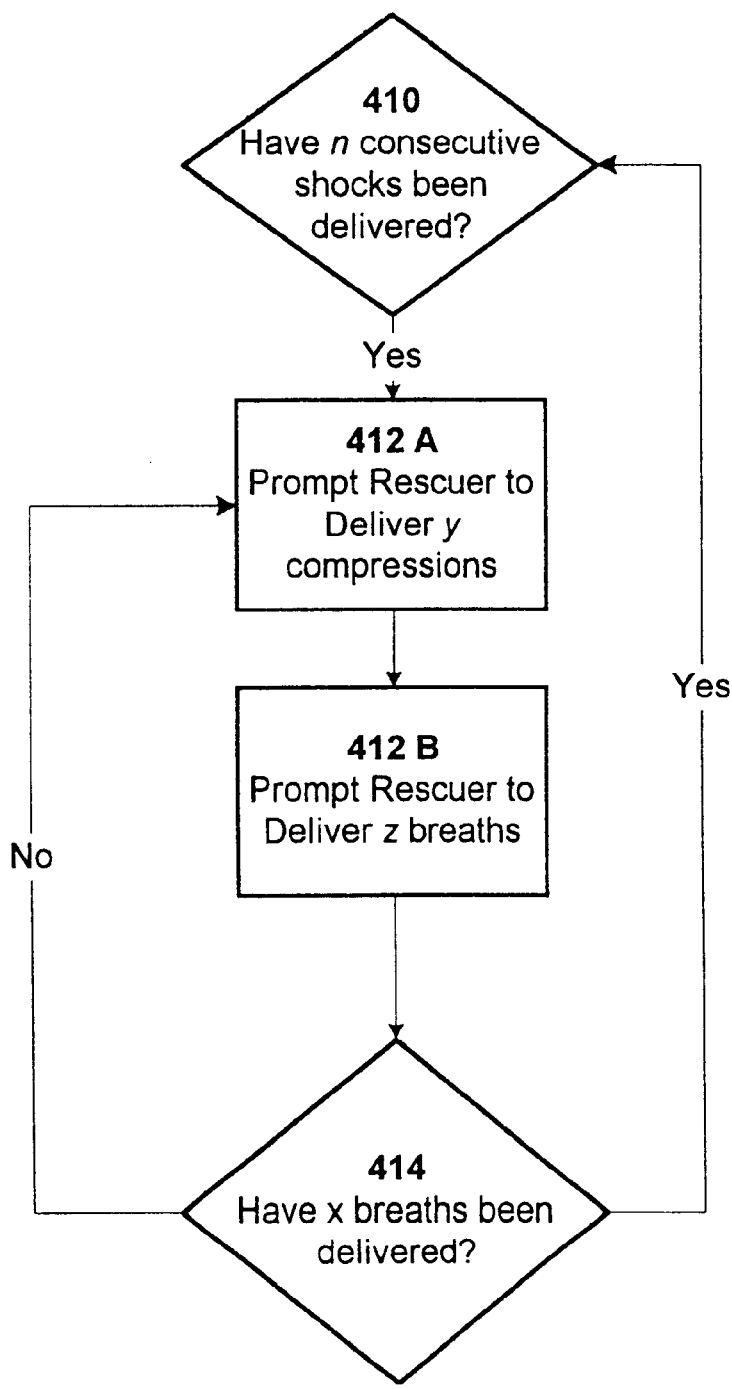
FIG. 10 is a flow chart demonstrating a defibrillator operating to deliver CPR prompts for a set number of breaths according to an alternative method of this invention.

FIG. 10 is an example of a defibrillator operation method according to this invention. The defibrillator 10 determines the number of consecutive shocks that have been delivered 410. Once n consecutive shocks have been delivered, the defibrillator 10 instructs the rescuer in the protocol for administering CPR (the "CPR prompt mode" of "CPR instruct mode") 412.

During the CPR instruct mode 412, the defibrillator 10 instructs the rescuer to deliver y compressions 412 A, where y is a number preprogrammed into the defibrillator 10. For example, y could be the number of compressions required under the AHA protocol for an adult or the number of compressions required by the protocol of a specific jurisdiction. Once the defibrillator has instructed the rescuer to deliver y compressions 412 A, the defibrillator 10 instructs the rescuer to delivery z breaths 412 B. For example, z could be the number of breaths required under the AHA protocol for an adult. The sequence of delivering y compressions and z breaths is repeated until a total of x breaths have been delivered 414 during a CPR prompt mode, where x the total number of breaths in the protocol that the device has been programmed to follow during a CPR prompting period.

For example, a protocol could be programmed where y is 10 and z is 2 (10 compressions to 2 breaths) and x is 10, thus requiring the steps of 412 A and 412 B to be repeated until a total of 10 breaths had been delivered during that particular CPR prompting period.

Variations in the CPR protocol, including the addition of prompting steps, is within the scope of this invention. More specific examples of possible embodiments of the prompting steps are discussed in more detail below.

Once CPR has been delivered for the programmed number of breaths 414, the defibrillator 10 returns to counting the number of consecutive shocks administered 410.

Figure 11:
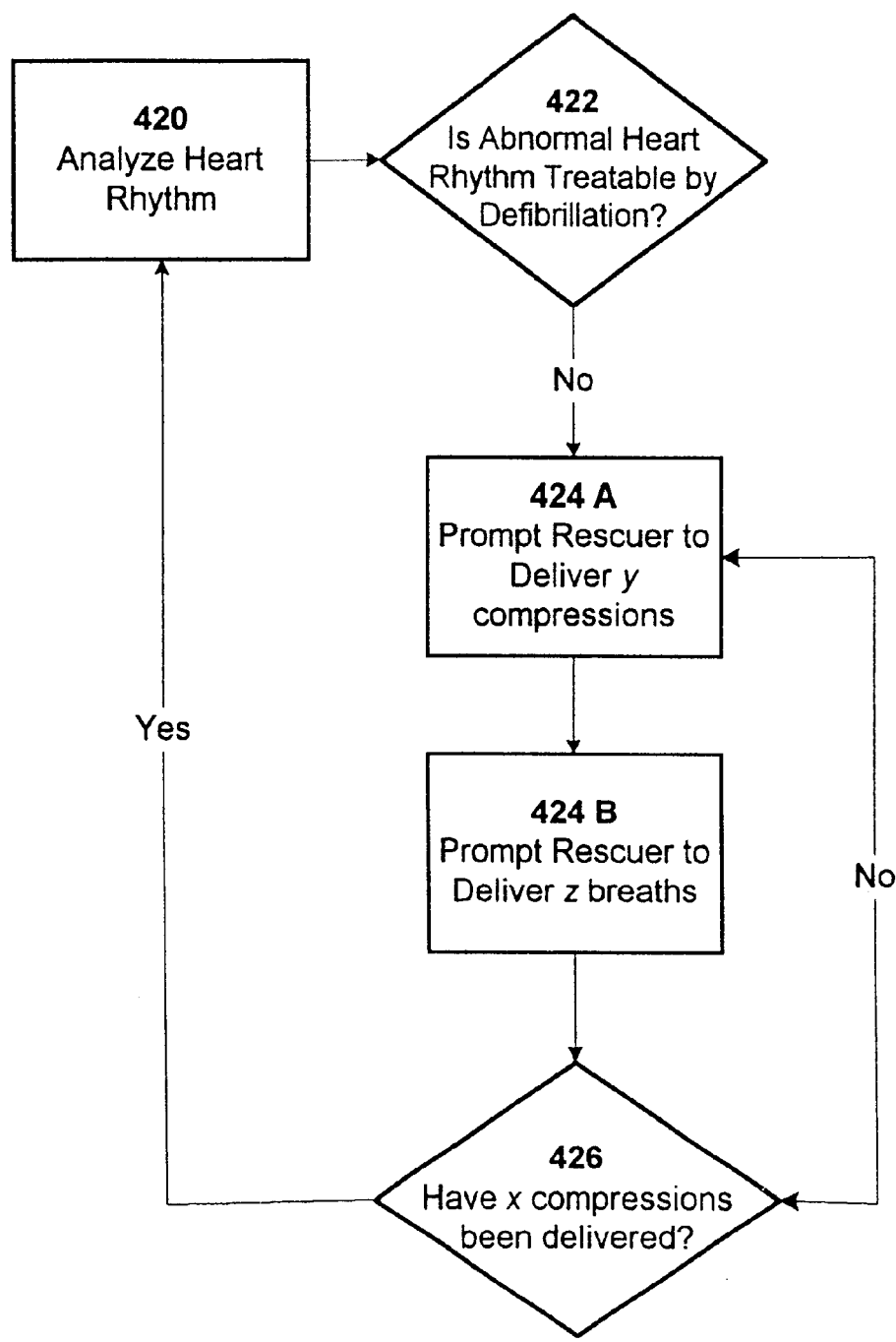
FIG. 11 is a flow chart demonstrating a defibrillator operating to deliver CPR prompts for a set number of compressions according to an alternative method of this invention. The step of analyzing the heart rhythm is included.

FIG. 11 is another example of a defibrillator operation method according to this invention. The defibrillator analyzes the heart rhythm 420 and determines whether the heart rhythm is shockable (i.e., is treatable by the administration of a defibrillating shock) 422. The heart rate analyzed by the defibrillator may be real-time data from an actual patient receiving treatment, or may be simulated or historical data used for purposes of training. If the heart rhythm is abnormal but is not treatable by defibrillation, the defibrillator 10 instructs the rescuer in the correct protocol for administering CPR.

During the CPR instruct mode, the defibrillator 10 instructs the rescuer to deliver y compressions 424 A, where y is a number preprogrammed into the defibrillator 10. For example, y could be the number of compressions required under the AHA protocol for an adult. Once the defibrillator has instructed the rescuer to deliver y compressions 424 A, the defibrillator 10 instructs the rescuer to deliver z breaths 424 B. For example, z could be the number of breaths required under the AHA protocol for an adult. The sequence of delivering y compressions and z breaths is repeated until x compressions have been delivered 426, where x is the total number of compressions in the protocol that the device has been programmed to follow during a CPR prompting period.

For example, a protocol could be programmed where y is 5 and z is 1 (5 compressions to 1 breath) and x is 25, thus requiring the steps of 424 A and 424 B to be repeated until a total of 25 compressions had been delivered during that particular CPR prompting period.

Additional prompting steps or other variations in this protocol are within the scope of the invention. More specific examples of possible embodiments of the prompting steps are discussed in more detail below.

Once CPR has been delivered for the programmed number of compressions 426, the defibrillator 10 returns to analyzing the heart rhythm 420.

Figure 12:
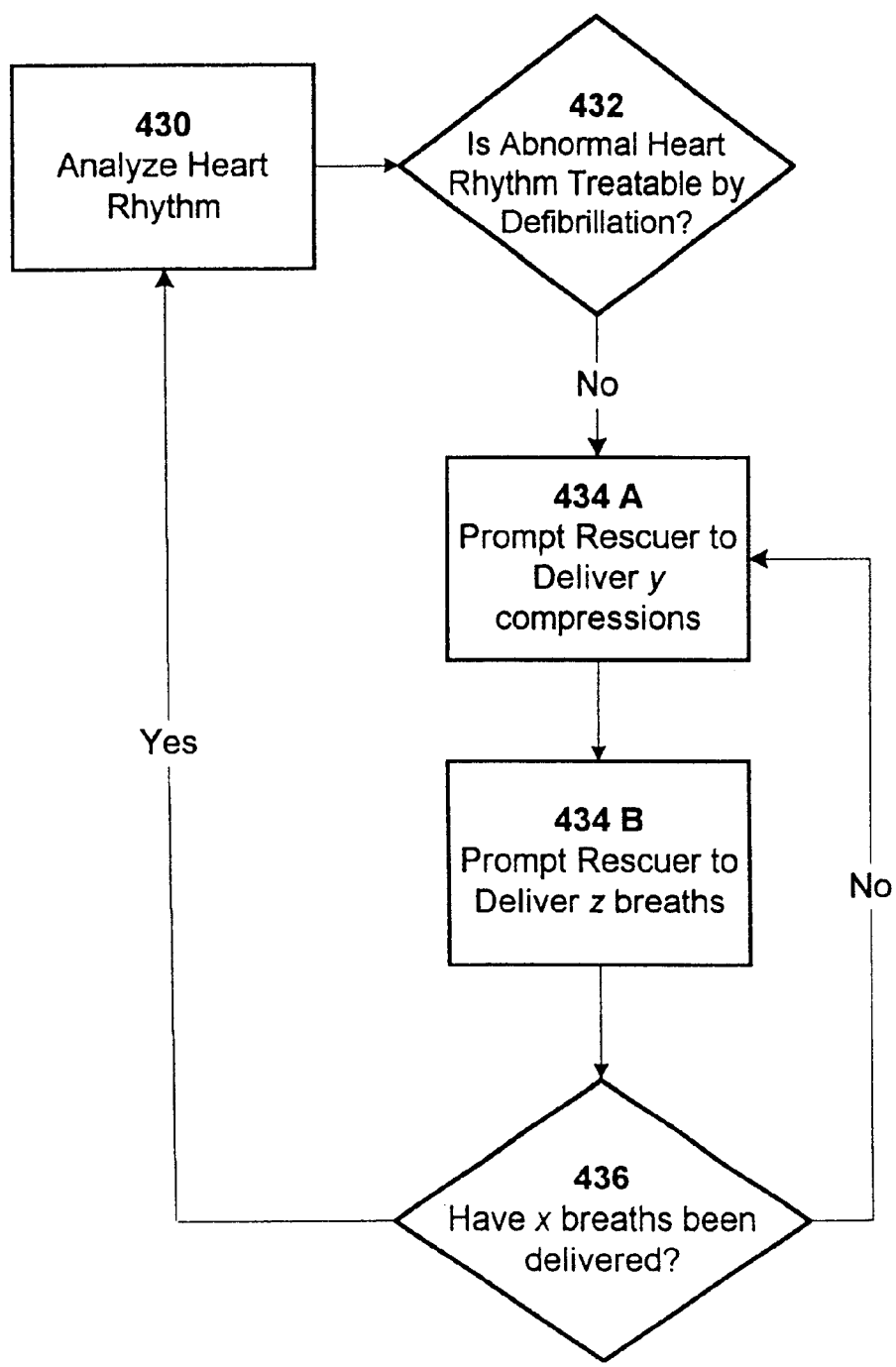
FIG. 12 is a flow chart demonstrating a defibrillator operating to deliver CPR prompts for a set number of breaths according to an alternative method of this invention. The step of analyzing the heart rhythm is included.

FIG. 12 is another example of a defibrillator operation method according to this invention. The defibrillator analyzes the heart rhythm 430 and determines whether the heart rhythm is shockable (i.e., is treatable by the administration of a defibrillating shock) 432. The heart rate analyzed by the defibrillator may be real-time data from an actual patient receiving treatment, or may be simulated or historical data used for purposes of training. If the heart rhythm is abnormal but is not treatable by defibrillation, the defibrillator 10 instructs the rescuer in the correct protocol for administering CPR.

During the CPR instruct mode, the defibrillator 10 instructs the rescuer to deliver y compressions 434 A, where y is a number preprogrammed into the defibrillator 10. For example, y could be the number of compressions required under the AHA protocol for an adult. Once the defibrillator has instructed the rescuer to deliver y compressions 434 A, the defibrillator 10 instructs the rescuer to delivery z breaths 434 B. For example, z could be the number of breaths required under the AHA protocol for an adult. The sequence of delivering y compressions and z breaths is repeated until x breaths have been delivered 436, where x is the total number of breaths in the protocol that the device has been programmed to follow during a CPR prompting period.

For example, a protocol could be programmed where y is 10 and z is 2 (10 compressions to 2 breaths) and x is 10, thus requiring the steps of 434 A and 434 B to be repeated until a total of 10 breaths had been delivered during that particular CPR prompting period.

Additional prompting steps or other variations in this protocol are within the scope of the invention. More specific examples of possible embodiments of the prompting steps are discussed in more detail below.

Once CPR has been delivered for the programmed number of breaths 436, the defibrillator 10 returns to analyzing the heart rhythm 430.

Other methods of determining the length and timing of the CPR instructions could also be used and are within the scope of this invention. For example, the defibrillator could be programmed to deliver CPR until a total number of breaths and compressions had been administered prior to returning to the shocking or analyzing phase. Alternatively, the defibrillator could be programmed to deliver CPR until a total number of sequences of breaths to compressions had been delivered prior to returning to the shocking or analyzing phase. Specifically, the defibrillator could be instructed to administer, for example, 5 sequences of 10 compressions to 2 breaths.

Typically, the protocol for CPR will be pre-programmed into the defibrillator 10 prior to placing the defibrillator 10 into service. The pre-programmed protocol may be the AHA protocol, used above for illustration purposes and shown in FIGS. 5–8, or may be any other protocol followed by the rescuer or the organization that controls the operation of the defibrillator. Additionally, the CPR prompt mode may provide additional steps. For example, the protocol may allow the rescuer to input data as to the number of rescuers and the relative age of the patient, in order to allow the defibrillator 10 to select the correct CPR prompting protocol where the protocol varies, for age, etc. The protocol may also direct the rescuer to, for example, "call 911" or "clear airway." Additionally, the protocol may include audible or visual prompts directing the rescuer to, for example, look-listen-and-feel for breaths, or to check the patient's pulse for 10 seconds.

Figure 13:
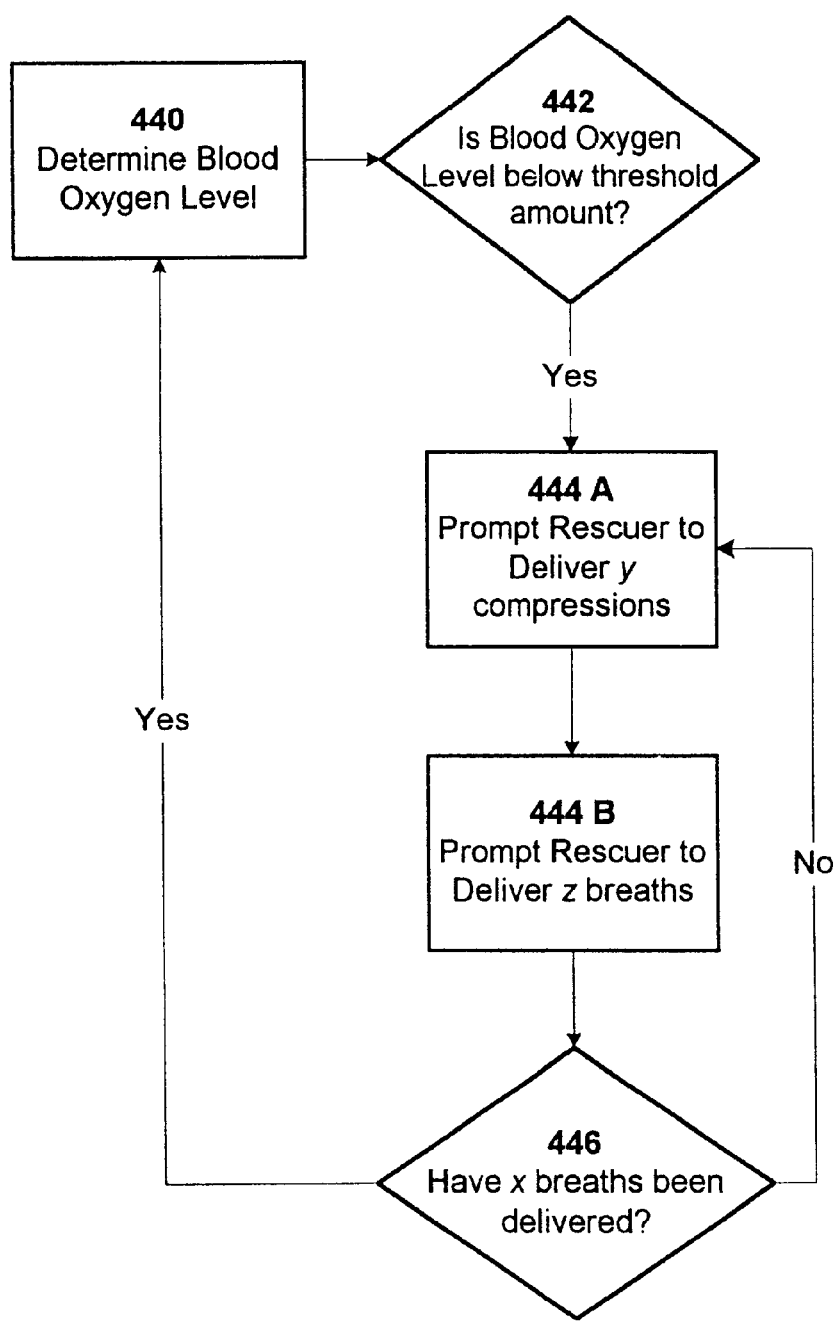
FIG. 13 is a flow chart demonstrating a defibrillator operating to deliver CPR prompts for a set number of breaths according to an alternative embodiment of this invention. The step of determining blood oxygen level is included.

FIG. 13 is an example of a defibrillator operation method according to this invention. The defibrillator 10 determines whether the blood oxygen level is below a threshold amount 442 using information obtained from one of the data gathers 28. Once the blood oxygen level has fallen below a threshold amount, the defibrillator 10 instructs the rescuer in the protocol for administering CPR (the "CPR prompt mode" or "CPR instruct mode") 444.

During the CPR instruct mode 444, the defibrillator 10 instructs the rescuer to deliver y compressions 444 A, where y is a number preprogrammed into the defibrillator 10. For example, y could be the number of compressions required under the AHA protocol for an adult or the number of compressions required by the protocol of a specific jurisdiction. Once the defibrillator has instructed the rescuer to deliver y compressions 444 A, the defibrillator 10 instructs the rescuer to deliver z breaths 444 B. For example, z could be the number of breaths required under the AHA protocol for an adult. The sequence of delivering y compressions and z breaths is repeated until a total of x breaths have been delivered 446 during a CPR prompt mode, where x the total number of breaths in the protocol that the device has been programmed to follow during a CPR prompting period.

For example, a protocol could be programed where y is 10 and z is 2 (10 compressions to 2 breaths) and x is 10, thus requiring the steps of 444 A and 444 B to be repeated until a total of 10 breaths had been delivered during that particular CPR prompting period.

Variations in the CPR protocol, including the addition of prompting steps, is within the scope of this invention. More specific examples of possible embodiments of the prompting steps are discussed in more detail below.

Once CPR has been delivered for the programmed number of breaths 446, the defibrillator 10 returns to determining the blood oxygen level 440.

Figure 14:
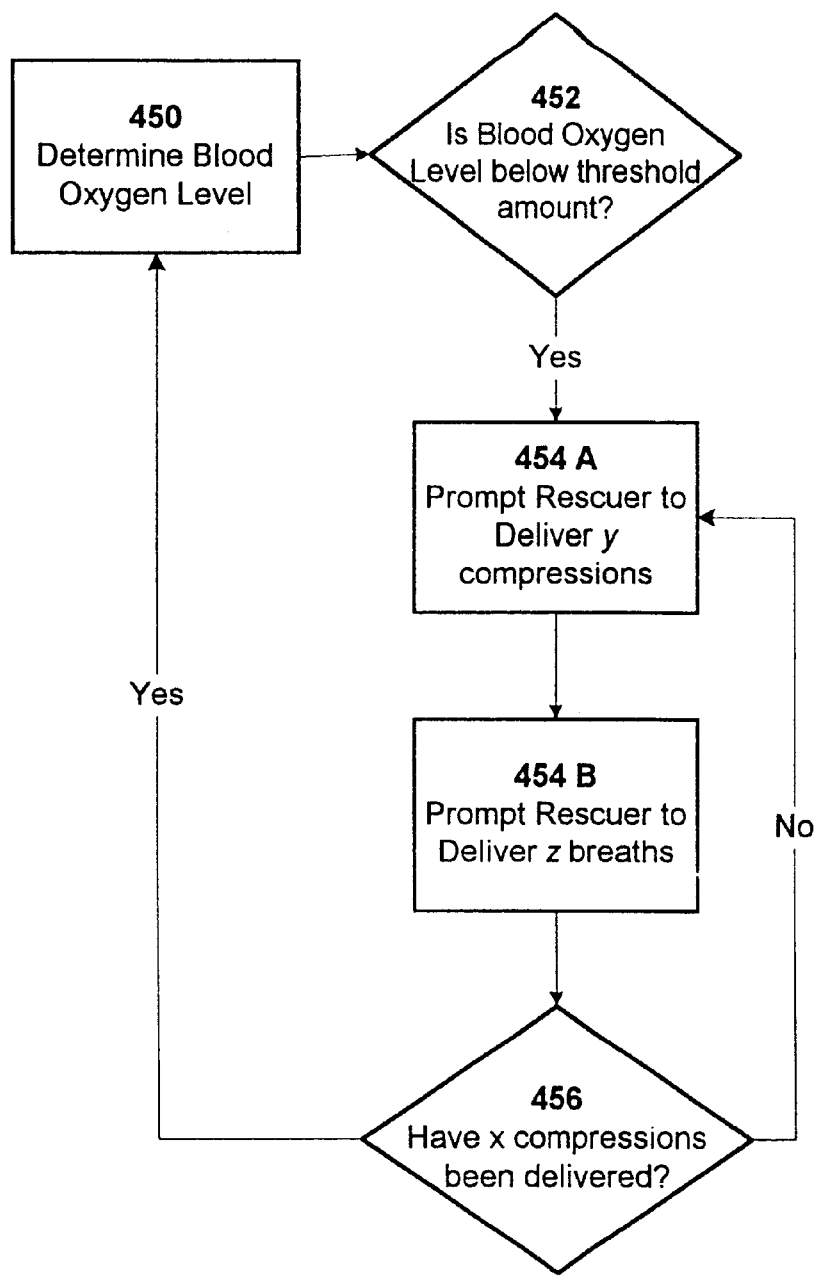
FIG. 14 is a flow chart demonstrating a defibrillator operating to deliver CPR prompts for a set number of compressions according to an alternative embodiment of this invention. The step of determining blood oxygen level is included.

FIG. 14 is an example of defibrillator operation method according to this invention. The defibrillator 10 determines whether the blood oxygen level is below a threshold amount 452 using information obtained from one of the data gathers. Once the blood oxygen level has fallen below a threshold amount, the defibrillator 10 instructs the rescuer in the protocol for administering CPR (the "CPR prompt mode" or "CPR instruct mode") 454.

During the CPR instruct mode 454, the defibrillator 10 instructs the rescuer to deliver y compressions 454 A, where y is a number preprogrammed into the defibrillator 10. For example, y could be the number of compressions required under the AHA protocol for an adult or the number of compressions required by the protocol of a specific jurisdiction. Once the defibrillator has instructed the rescuer to deliver y compressions 454 A, the defibrillator 10 instructs the rescuer to deliver z breaths 454 B. For example, z could be the number of breaths required under the AHA protocol for an adult. The sequence of delivering y compressions and z breaths is repeated until a total of x compressions have been delivered 456 during a CPR prompt mode, where x the total number of compressions in the protocol that the device has been programmed to follow during a CPR prompting period.

For example, a protocol could be programmed where y is 10 and z is 2 (10 compressions to 2 breaths) and x is 50, thus requiring the steps of 454 A and 454 B to be repeated until a total of 50 compressions had been delivered during that particular CPR prompting period.

Variations in the CPR protocol, including the addition of prompting steps, is within the scope of this invention. More specific examples of possible embodiments of the prompting steps are discussed in more detail below.

Figure 15:
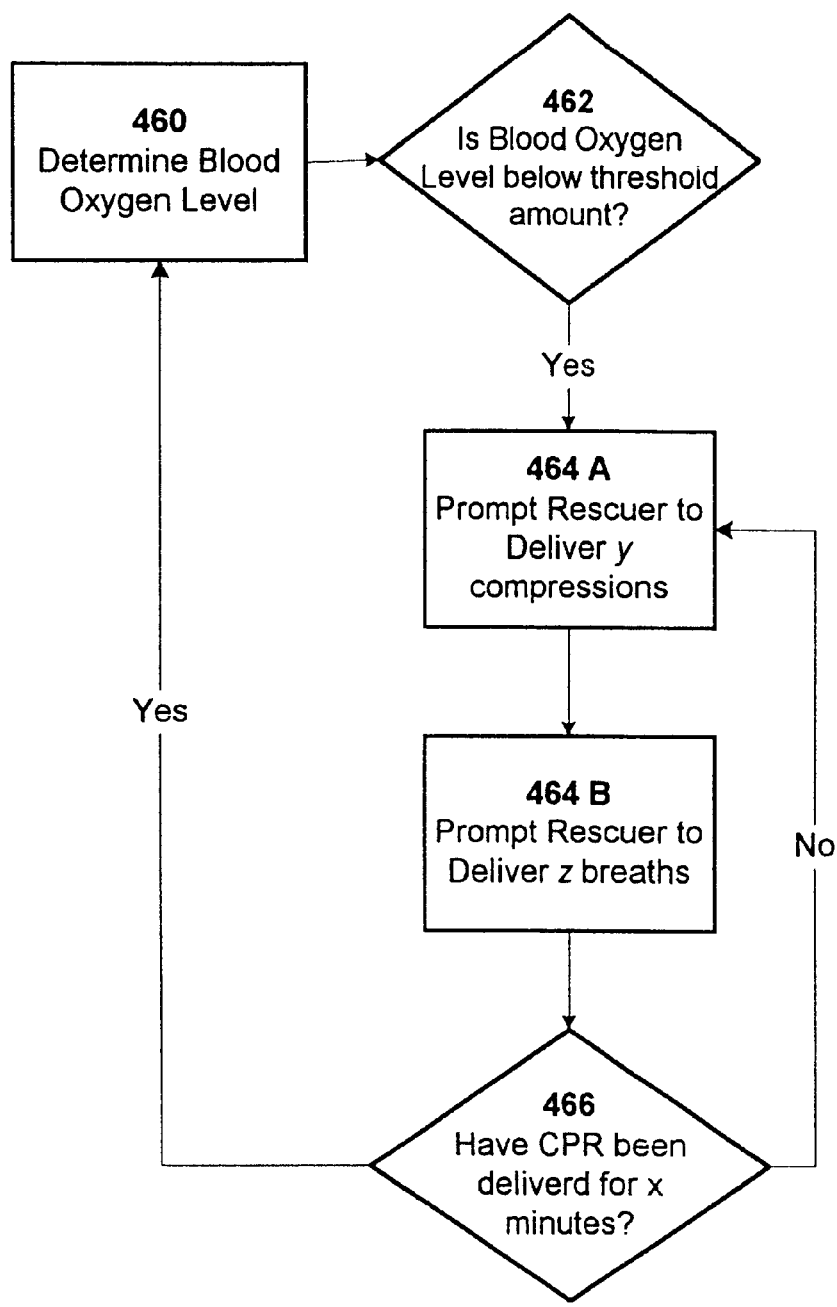
FIG. 15 is a flow chart demonstrating a defibrillator operating to deliver CPR prompts for a set amount of time according to an alternative embodiment of this invention. The step of determining blood oxygen level is also included.

FIG. 15 is an example of a defibrillator operation method according to this invention. The defibrillator 10 determines whether the blood oxygen level is below a threshold amount 462 using information obtained from one of the data gathers. Once the blood oxygen level has fallen below a threshold amount, the defibrillator 10 instructs the rescuer in the protocol for administering CPR (the "CPR prompt mode" or "CPR instruct mode") 464.

During the CPR instruct mode 464, the defibrillator 10 instructs the rescuer to deliver y compressions 464 A, where y is a number preprogrammed into the defibrillator 10. For example, y could be the number of compressions required under the AHA protocol for an adult or the number of compressions required by the protocol of a specific jurisdiction. Once the defibrillator has instructed the rescuer to deliver y compressions 464 A, the defibrillator 10 instructs the rescuer to deliver z breaths 464 B. For example, z could be the number of breaths required under the AHA protocol for an adult. The sequence of delivering y compressions and z breaths is repeated until a total of x time has passed 466 during a CPR prompt mode, where x the amount of time the device has been programmed to follow during a CPR prompting period.

For example, protocol could be programmed where y is 10 and z is 2 (10 compressions to 2 breaths) and x is 1 minute, thus requiring the steps of 464 A and 464 B to be repeated until a 1 minute had passed for that particular CPR prompting period.

Variations in the CPR protocol, including the addition of prompting steps, is within the scope of this invention. More specific examples of possible embodiments of the prompting steps are discussed in more detail below.

Once CPR has been delivered for the programmed period of time 466, the defibrillator 10 returns to determining the blood oxygen level 460.

Figure 18:
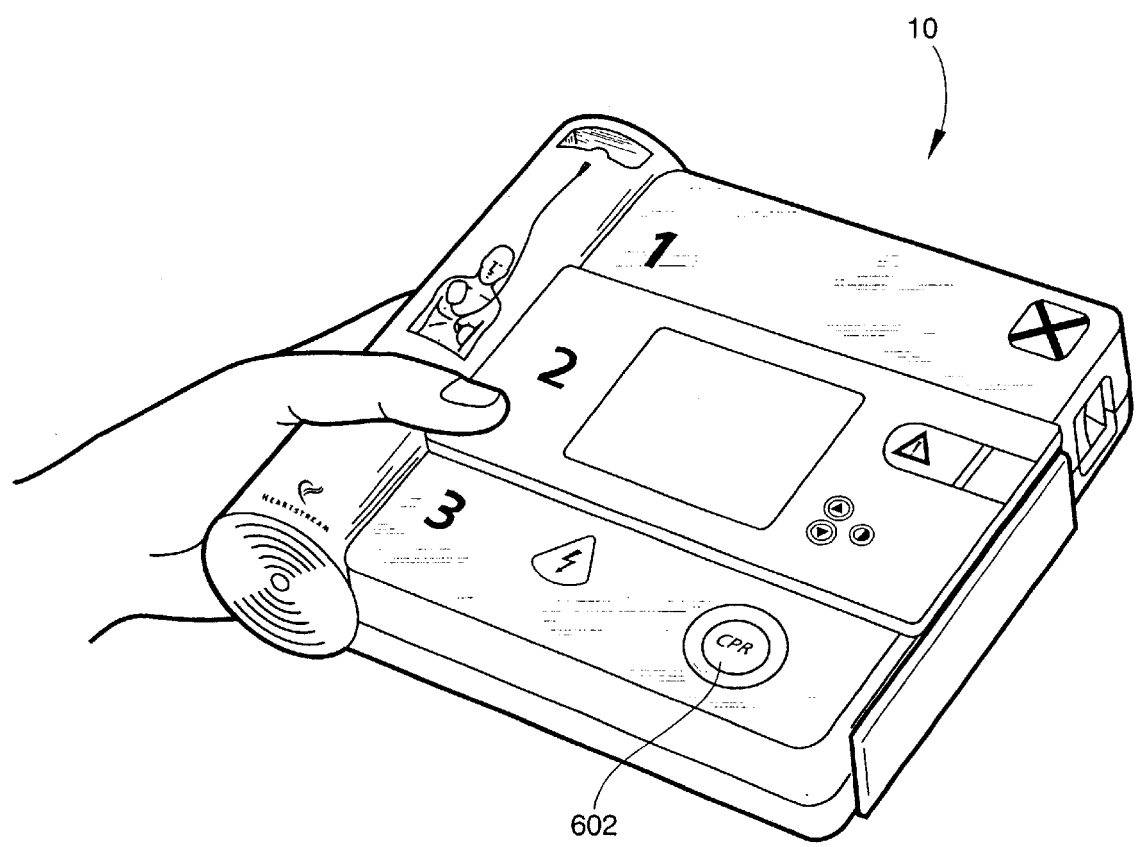
FIG. 18 is a top elevational view of a defibrillator for use with this invention.

The embodiments described and shown in FIGS. 3–15 provide for automatic activation of the CPR prompts based on meeting pre-set conditions. In another embodiment, a defibrillator is provided that allows the operator to begin CPR prompts on demand. By allowing the operator to begin administering CPR out of sequence, or on demand, CPR can also be administered when the operator believes the victim requires CPR. For example, using the defibrillator shown in FIG. 18, the operator could press button 602 to interrupt the performance of the algorithm and immediately begin CPR prompting. Once the on demand CPR instructions have been delivered, the defibrillator would then return to the CPR administration sequence it had been programmed to follow, such as those shown in FIGS. 3–15.

Figure 16A:
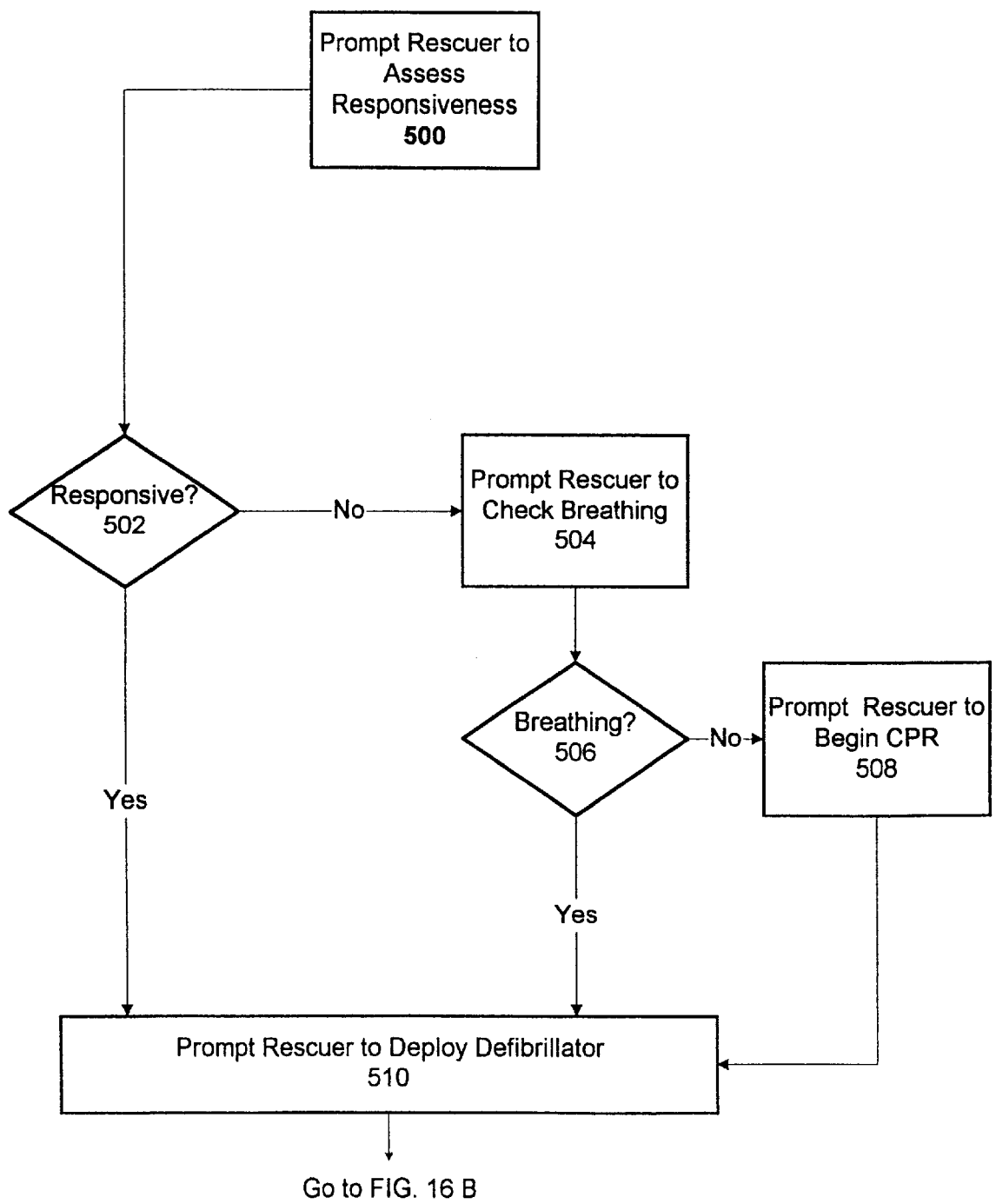
FIGS. 16A and B is a flow chart demonstrating a defibrillator operating according to an alternative method of this invention to delivery ACLS prompts to a user for an adult victim.
Figure 16B:
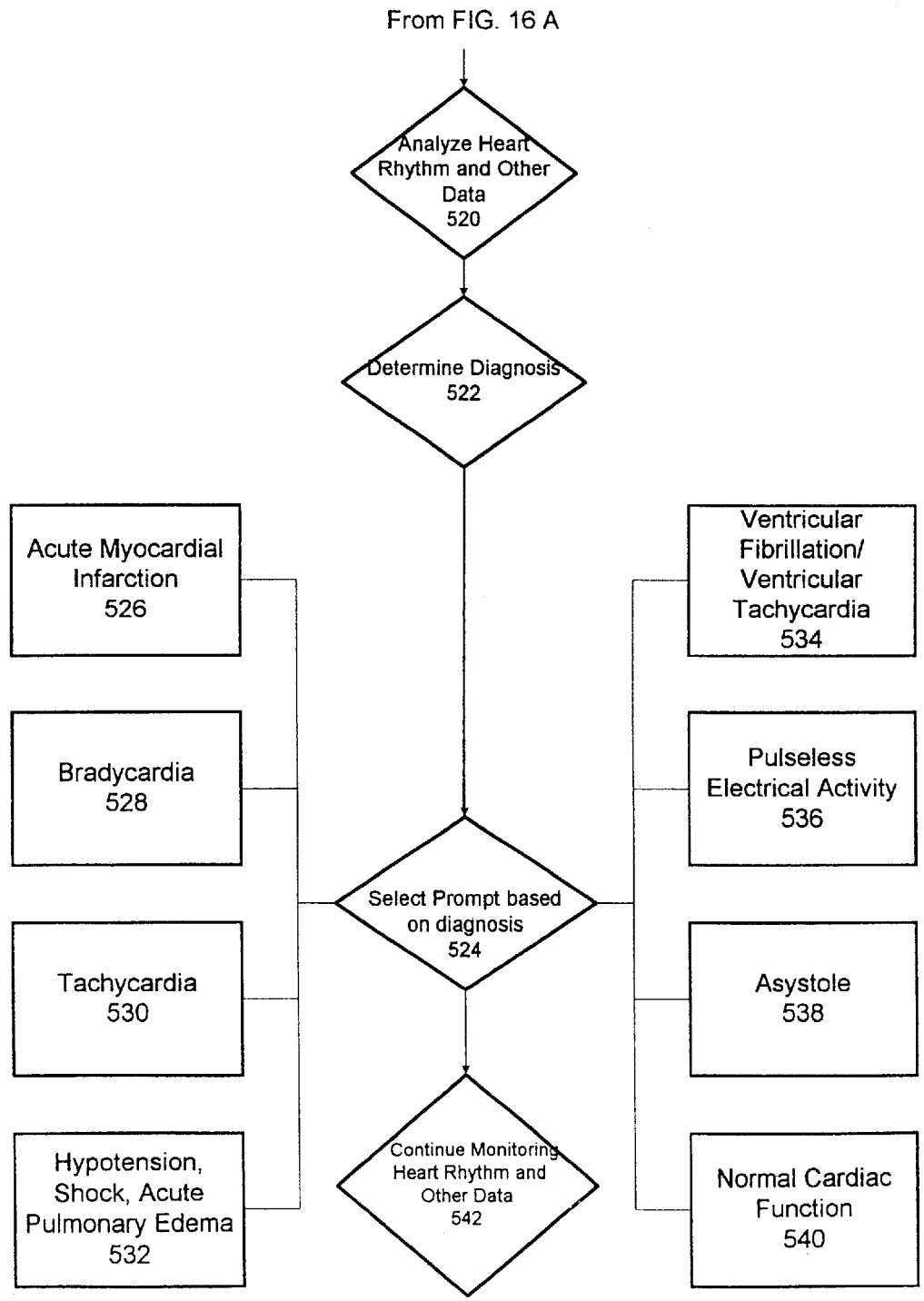

FIGS. 16A and B are directed to a defibrillator operation method that includes the delivery of ACLS prompts for an adult patient.

FIG. 16A demonstrates a defibrillator operation method where the defibrillator 10 prompts the rescuer to assess the responsiveness of the victim 500. As discussed above, the rescuer may indicate the victim's responsiveness by, for example, pressing a button, or by responding, where voice recognition software is employed.

If the victim is responsive, the defibrillator then prompts the rescuer to deploy the defibrillator 510. Instructions to deploy the defibrillator could be followed by more detailed instructions such as "attach pads" or "connect electrode". If the victim is not responsive then the defibrillator prompts the rescuer to check breathing 504. The rescuer may indicate whether the victim is breathing by, for example, pressing a button, or by responding, where voice recognition software is employed. If the victim is breathing, then the defibrillator 10 prompts the rescuer to deploy the defibrillator 510. However, if the victim is not breathing, the defibrillator prompts the rescuer to begin CPR 508.

Following the prompt to begin CPR 508, the instruction generator may follow a detailed CPR instruction protocol such as those shown in FIGS. 3–15. The amounts of prompting provided by the defibrillator will depend upon the set-up selected prior to deployment of the defibrillator.

Once the rescuer has been prompted to deploy the defibrillator, and the defibrillator is deployed, the defibrillator will analyze the heart rhythm and any other data that may be received relative to the cardiac emergency 520. Such additional information could be, for example, information received from the data gatherers 28, such as a pulse oximeter, a pulse detector, a blood pressure detector, or a hemodynamic monitor. When some or all data gatherers are not available, the defibrillator may prompt the user to input information regarding various physiological parameters relating to the victim's condition. Regardless of how the information is obtained, the defibrillator will analyze the information in conjunction with the heart rhythm to determine a treatment protocol.

Except during the delivery of CPR, the defibrillator will continue to monitor the heart rhythm and other data while the specific treatment instructions are given to the rescuer. It is important to note that if any of the parameters affecting the treatment decision selected at 522 change during the course of the treatment, the defibrillator will pause prompting the rescuer to re-evaluate the patient data, and make a new diagnosis, and will then begin prompting the rescuer to administer care based on the revised diagnosis.

The diagnosis made by the defibrillator may fall into the following categories: acute myocardial infarction 526; bradycardia 528; tachycardia 530; hypotension, shock, acute pulmonary edema 532; VF/shockable VT 534; PEA 536; asystole 538; and normal cardiac function 540. The treatment algorithm followed for each of these possible diagnoses will depend on several factors. For example, the level of experience of the rescuer, the amount of equipment or drugs available, and the protocol followed by the agency or operator of the defibrillator. Obviously, for a lay person, such as a police officer or a flight attendant, the level of prompting would likely be more detailed than the prompting for an EMT or physician. Also, the level of prompting used during training can vary depending on the level of skill of the person being trained or the ultimate level of skill that is desired. Additionally, where the agency controlling the operation of the defibrillator is placing the defibrillator into service where specific procedures cannot be performed (for example, where the requisite equipment is not available) these prompts may be removed from the protocol. Finally, the controlling organization may have specific protocols that are followed that vary from the standard treatment algorithms discussed below.

For purposes of illustration the examples of prompting routines described below, for the diagnoses 526–540, follow the recommended treatment procedures outlined in Emergency Cardiac Care Committee, et al., "III. Adult Advanced Cardiac Life Support" JAMA 268:2172–2183 (1992). Other variations or treatment protocols may be employed and are within the scope of the invention, although not described at length herein.

Where the defibrillator has determined that the appropriate diagnosis is acute myocardial infarction 526, the defibrillator could, for example, prompt the rescuer to "provide treatment for myocardial infarction". Alternatively, the defibrillator could provide more detailed instructions or suggestions to the rescuer, such as "administer oxygen" or "administer nitroglycerin". If the defibrillator is deployed where intravenous ("IV") access is available, additional prompts for administering a morphine IV or a nitroglycerin IV may be provided. The level of detail of the prompts can be pre-programmed to take into consideration the equipment available and the level of skill of the rescuer.

If, during the myocardial infarction 526 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . ."

Where the defibrillator has determined that the diagnosis is bradycardia 528, the defibrillator could, for example, prompt the rescuer to "provide treatment for bradycardia." Alternatively, the defibrillator could provide more detailed instructions such as "assess ABCs, secure airway, administer oxygen, start IV." In order to determine the next step to follow, the defibrillator must known whether there are serious signs or symptoms along with the bradycardia. At this point, the defibrillator may request user interaction to indicate the level of seriousness of the bradycardia. This may be accomplished by asking the user a series of questions relating to the symptoms, monitoring the symptoms using the data gatherers, or requesting the rescuer to input a yes/no response to indicate whether there are, for example, serious signs or symptoms.

If, during the bradycardia 528 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . ."

Where there are serious signs or symptoms along with the bradycardia, the defibrillator could prompt the rescuer to "deliver the intervention sequence: Atropine, TCP, Dopamine, Epinephrine and isoproterenol." The actual recommendation for drug delivery may vary depending upon the nature of the bradycardia. For example, atropine is the first pharmacologic agent recommended. However, atropine may exacerbate ischemia or induce VT, VF or both in cases where bradycardia is accommpanied by acute MI. Additionally, lidocaine may be lethal if the bradycardia is actually a ventricular escape rhythm.

If the bradycardia symptoms are not serious, the defibrillator could prompt the user to either "observe the patient" or "prepare for transvenous pacer" (where Type II second- or third-degree A V block is suspected).

If, during the bradycardia 528 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . "

Where the defibrillator has determined that the appropriate diagnosis is tachycardia 530, the defibrillator could prompt the rescuer "provide treatment for tachycardia." Alternatively, the defibrillator could provide more detailed instructions such as "assess ABCs, secure airway, administer oxygen, start IV." Additionally, the defibrillator could advise the rescuer to provide treatment for tachycardia and then inform the rescuer of the nature of the tachycardia (e.g., atrial fibrillation/flutter, paroxysmal supraventricular tachycardia ("PSVT"), wide complex tachycardia of uncertain type, or shockable VT ("CT")). If desired, the defibrillator could advise the rescuer to begin the appropriate treatment sequence for the particular type of tachycardia. Where atrial fibrillation/flutter has been detected, the defibrillator could instruct the rescuer to "consider diltiazem, β-blockers, verapamil, digoxin, procainamide, quinindine, or anticoagulants." Where PSVT has been detected, the defibrillator may instruct the rescuer to "perform vagal maneuvers" followed by "administer adenosine." If the defibrillator then detects a wide complex width, the defibrillator may then instruct the rescuer to "deliver lidocaine", followed by an instruction to "deliver procainamide." If the defibrillator determines that the lidocaine, procainamide treatment was not effective, and the victim is still suffering from wide-complex tachycardia, the defibrillator may then begin prompting the user to deliver synchronized cardioversion. Alternatively, where a narrow complex width is detected along with low or unstable blood pressure, the defibrillator will begin instructing the rescuer to deliver synchronized cardioversion. If, however, the narrow complex width accompanies normal or elevated blood pressure, the defibrillator may instruct the user to "deliver two sequential doses of verapamil over thirty minutes", followed by "consider digoxin, β-blockers, and diltiazem." If this treatment sequence fails, the defibrillator may then instruct the rescuer to deliver synchronized cardioversion. Where wide-complex tachycardia of an uncertain type has been detected, the defibrillator may instruct the rescuer to "deliver two sequences of lidocaine IV push every 5–10 minutes followed by adenosine rapid IV pushes every 1–2 minutes." Where the diagnosis is VT, the defibrillator may instruct the rescuer to delivery lidocaine every 5–10 minutes followed by procainamide, then bretylium. If these treatments are not effective, the defibrillator may then being instructing the rescuer to deliver synchronized cardioversion. Additionally, a counter or timer within the defibrillator may prompt the rescuer to deliver drugs at appropriate intervals subsequent to the first administration.

If, during the tachycardia 530 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . ."

Where the defibrillator has determined that the appropriate diagnosis is hypotension, shock, or acute pulmonary edema 532, the defibrillator could prompt the rescuer to "provide treatment for hypotension, shock, or acute pulmonary edema." Alternatively, the defibrillator could provide more detailed instructions such as "assess ABCs, secure airway, administer oxygen, start IV." At this point the defibrillator may either determine the nature of the problem or request the rescuer to indicate the nature of the problem. Where the problem is a "volume problem" (hypovolemia), the defibrillator could prompt the rescuer to "administer fluids" or "administer blood transfusions." The defibrillator may then instruct the rescuer to "take cause-specific interventions." Such cause specific interventions are directed to the cause of the volume problem, for example, treating the hemorrhage, gastrointestinal loss, renal loss, or adrenal insufficiency. Additionally, the defibrillator may instruct the rescuer to "consider vasopressors, if indicated." The defibrillator may periodically request that the rescuer indicate the blood pressure of the victim, or may monitor the blood pressure of the victim while the prompts for treating a volume problem are being administered. If the blood pressure indicates that there is a pump problem (cardiogenic),the defibrillator will then begin prompting the user to administer treatment for a pump problem. Where the systolic blood pressure is <70 mm Hg, the defibrillator may prompt the rescuer to "consider norepinephrine or dopamine." Where the systolic blood pressure is between 70–100 mm Hg, then the defibrillator could prompt the rescuer to "deliver dopamine and add norepinephrine." Where the systolic blood pressure is >100 mm Hg, then the defibrillator could prompt the rescuer to "administer dobutamine," followed by "consider further action if the patient is in acute edema." Such further actions could be specifically stated, if desirable. Finally, where the diastolic pressure is >110 mm Hg, the defibrillator could prompt the rescuer to "deliver nitroglycerine and/or nitroprusside." If the nature of the problem is a rate problem, the defibrillator will then prompt the rescuer to deliver the treatment protocol for bradycardia 528 (if the rate is too slow) discussed above, or tachycardia 530 (if the rate is too fast) also discussed above.

If, during the hypotension, shock, or acute pulmonary edema 532 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . "

Where the defibrillator has determined that the appropriate diagnosis is VF or shockable VT.534, the defibrillator could prompt the rescuer to "provide treatment for VF or shockable VT." Alternatively, the defibrillator could provide more detailed instructions such as "assess ABCs, perform CPR until defibrillator is attached." Thereafter, the defibrillator would revert to prompting the rescuer to deliver a CPR:shock protocol, such as the ones described in detail above and shown in FIGS. 3–14.

If, during the VF or shockable VT 534 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . ."

Where the defibrillator has determined that the appropriate diagnosis is PEA 536, the defibrillator could prompt the rescuer to "provide treatment for PEA." Alternatively, the defibrillator could provide more detailed instructions such as "continue CPR, intubate at once, obtain IV access and assess blood flow." The prompts could be repeated once followed by a pause to allow the rescuer to perform the action, or could pause until the rescuer indicates either vocally, or by pressing a button, that the procedure has been completed and the rescuer is ready for the next prompt. Following the initial prompts, the defibrillator could instruct the rescuer to consider possible causes. Alternatively, the defibrillator could assess the information provided by the data gatherers to determine possible causes. If the defibrillator or the operator determines that the cause is, for example a massive MI, then the defibrillator would switch the prompt protocol to the prompts for treating a MI 526, discussed above. In another example, the most common cause o electrical activity without a measurable blood pressure is hypovolemia. Where the PEA is detected along with a low blood volume, the defibrillator would revert to prompting the rescuer in the treatment protocol for hypotension, shock, or pulmonary edema 532, discussed above. Where the defibrillator or the operator are unable to determine a cause for PEA (which would direct the defibrillator to another treatment algorithm), the defibrillator may prompt the user to "deliver epinephrine and (if the rate is too slow) atropine." Epinephrine and atropine are the nonspecific interventions for PEA. The defibrillator may further instruct the rescuer to "deliver aggressive hypoventilation."

If, during the PEA 536 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . ."

Where the defibrillator has determined that the appropriate diagnosis is asystole 538, the defibrillator could prompt the rescuer to "provide treatment for asystole." Alternatively, the defibrillator could provide more detailed instructions such as "continue CPR, intubate at once, obtained IV access and confirm asystole in more than one lead." Following the initial prompt, the defibrillator could prompt the rescuer to "consider possible causes", or "consider immediate transcutaneous pacing." Thereafter, the defibrillator may prompt the rescuer to "deliver epinephrine" followed by "deliver atropine."

If, during the asystole 538 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . ."

Where the defibrillator has determined that there is normal cardiac function 540, the defibrillator could prompt the rescuer to "place the victim in the rescue position if there is no trauma."

If, during the normal cardiac function 540 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . ."

Figure 17A:
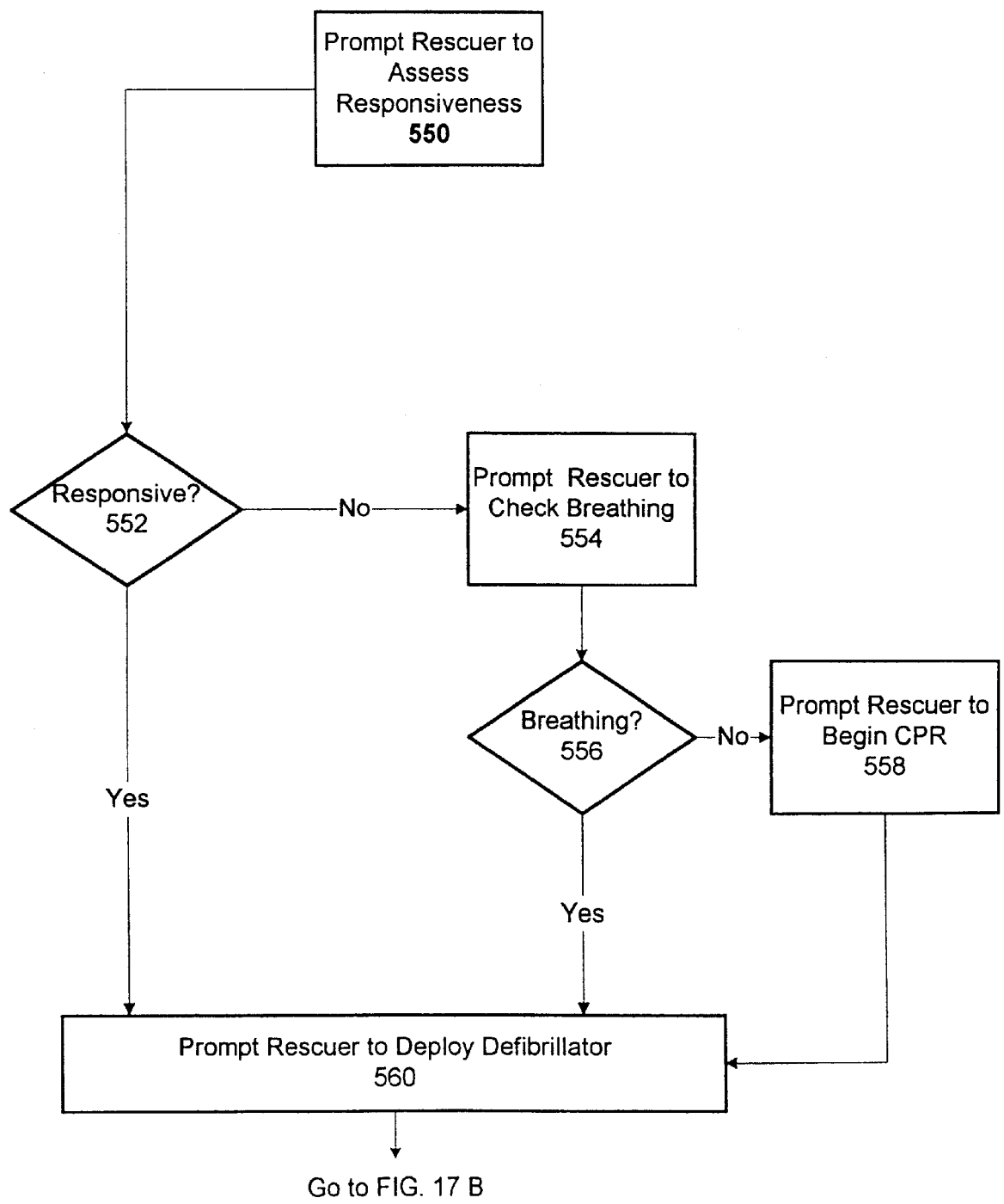
FIGS. 17A and B is a flow chart demonstrating a defibrillator operating according to an alternative method of this invention to deliver ACLS prompts to a user for a pediatric victim.
Figure 17B:
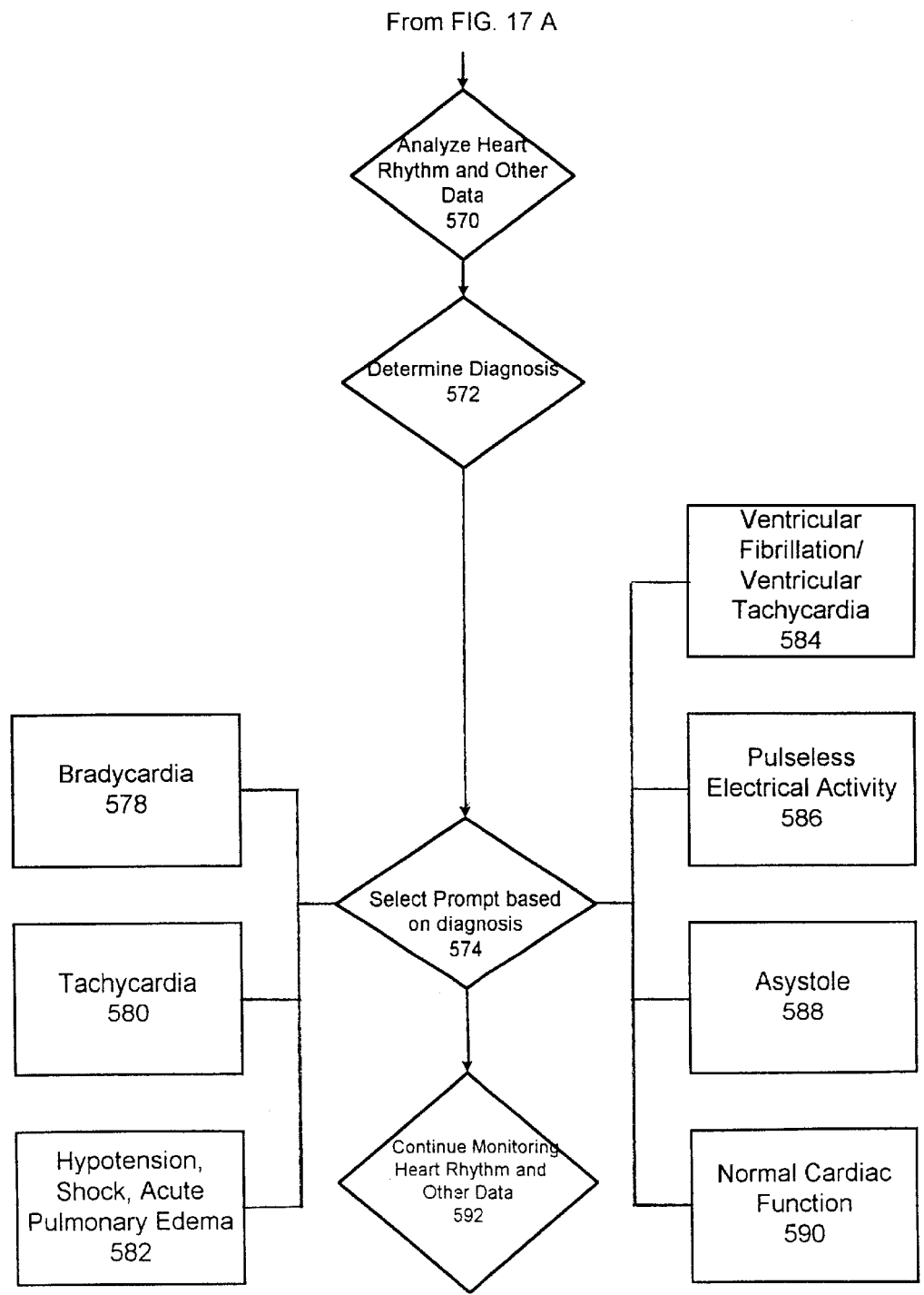

FIGS. 17A and B are directed to a defibrillator operation method that includes the delivery of ACLS prompts for a pediatric patient.

FIG. 17A demonstrates a defibrillator operation method when the defibrillator 10 prompts the rescuer to assess the responsiveness of the victim 550. As discussed above, the rescuer may indicate the victim's responsiveness by, for example, pressing a button, or by responding, where voice recognition software is employed.

If the victim is responsive, the defibrillator then prompts the rescuer to deploy the defibrillator 560. Instructions to deploy the defibrillator could be followed by more detailed instructions such as "attach pads" or "connect electrode". If the victim is not responsive, then the defibrillator prompts the rescuer to check breathing 554. The rescuer may indicate whether the victim is breathing by, for example, pressing a button, or by responding, where voice recognition software is employed. If the victim is breathing, then the defibrillator 10 prompts the rescuer to deploy the defibrillator 560. However, if the victim is not breathing, the defibrillator prompts the rescuer to begin CPR 558.

Following the prompt to begin CPR 558, the instruction generator may follow a detailed CPR instruction protocol such as those shown in FIGS. 3–15. The amount of prompting provided by the defibrillator will depend upon the set-up selected prior to deployment of the defibrillator. Once the rescuer has completed delivering CPR, the instruction generator will return to the method of FIG. 17A and instruct the rescuer to deploy the defibrillator 560.

It will be appreciated by those of skill in the art that the defibrillator may instruct the rescuer to attach the defibrillator at any point during the method, prior to proceeding with any other instructions.

Once the rescuer has been prompted to deploy the defibrillator, and the defibrillator is deployed, the defibrillator will analyzer the heart rhythm and any other data that may be received relative to the cardiac emergency 570. Such additional information could be, for example, information received from the data gatherers, such as a pulse oximeter, a pulse detector, a blood pressure detector, or a hemodynamic monitor. Where some or all data gatherers are not available, the defibrillator may prompt the user to input information regarding various physiological parameters relating to the victim's condition. Regardless of how the information is obtained, the defibrillator will analyze the information in conjunction with the heart rhythm to determine a treatment protocol.

Except during the delivery of CPR, the defibrillator will continue to monitor the heart rhythm and other data while the specific treatment instructions are given to the rescuer. It is important to note that if any of the parameters effecting the treatment decision selected at 572 change during the course of the treatment, the defibrillator will pause prompting the rescuer, re-evaluate the patient data, make a new diagnosis, and then begin prompting the rescuer to administer care based on the revised diagnosis.

The diagnosis made by the defibrillator may fall into the following categories: acute bradycardia 578; tachycardia 580; hypotension, shock, acute pulmonary edema 582; VF/shockable VT 584; PEA 586; asystole 588; and normal cardiac function 590. The treatment algorithm followed for each of these possible diagnoses will depend on several factors. For example, the level of experience of the rescuer, the amount of equipment or drugs available, and the protocol followed by the agency or operator of the defibrillator. Obviously, for a lay person, such as a police officer or a flight attendant, the level of prompting would likely be more detailed than the prompting for an EMT or physician. Also, the level of prompting used during training can vary depending on the level of skill of the person being trained or the ultimate level of skill that is desired. Additionally, where the agency controlling the operation of the defibrillator is placing the defibrillator into service where specific procedure cannot be performed (for example, where the requisite equipment is not available) these prompts may be removed from the protocol. Finally, the controlling organization may have specific protocols that are followed that vary from the standard treatment algorithms discussed below.

For purposes of illustration the examples of prompting routines described below, for the diagnoses 578–590, follow the recommended treatment procedures outlined in Pediatric Advanced Life Support "7. Cardiac Rhythm Disturbances" 1–15 (AHA, 1997). Other variations or treatment protocols may be employed and are within the scope of the invention, although not described at length herein.

Where the defibrillator has determined that the diagnosis is bradycardia 578, the defibrillator could, for example, prompt the rescuer to "provide treatment for bradycardia". Alternatively, the defibrillator could provide more detailed instructions such as "assess ABCs, secure airway, administer oxygen, assess vital signs." In order to determine the next step to follow, the defibrillator must know whether there is severe cardiorespiratory compromise. At this point, the defibrillator may request user interaction to indicate the level of seriousness of the bradycardia. This may be accomplished by asking the user a series of questions relating to the symptoms, monitoring the symptoms using the data gatherers, or requesting the rescuer to input a yes/no response to indicate whether there are, for example, serious signs or symptoms.

Where there is no severe cardiorespiratory compromise (e.g. perfusion is okay and there is no hypotension and no respiratory difficulty), the defibrillator could prompt the user to observe the patient and support the ABCs.

Where there is severe cardiorespiratory compromise, the defibrillator and could prompt the user to perform chest compressions if the heart rate is <60 beats/min. Additionally the defibrillator could prompt the rescuer to start IV/IO access. Once access is gained, the defibrillator could prompt the rescuer to administer 0.01 mg/kg of epinephrine every 3–5 minutes. A counter or timer on the defibrillator controller could monitor the amount of time since the last epinephrine dose and prompt the rescuer to deliver subsequent doses. Additionally, a prompt could be provided to administer atropine at 0.02 mg/kg (with a minimum dose of 0.1 mg and a maximum dose of 0.5 mg/kg). As with the epinephrine, the counter or timer could be employed to determine when a second dosage should be administered.

If, during the bradycardia 578 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . . "

Where the defibrillator has determined that the appropriate diagnosis is tachycardia 580, the defibrillator could prompt the rescuer "provide treatment for tachycardia," Alternatively, the defibrillator could provide more detailed instructions such as "assess and maintain airway, administer oxygen, ensure ventilation." Additionally, the defibrillator could advise the rescuer to provide treatment for tachycardia and then inform the rescuer of the nature of the tachycardia (e.g., sinus tachycardia, supraventricular tachycardia ("SVT"), or shockable VT). If desired, the defibrillator could advise the rescuer to begin the appropriate treatment sequence for the particular type of tachycardia.

Where the diagnosis is sinus tachycardia, the rescuer could be prompted to "identify and treat the possible causes." More detailed information about the causes could also be provided, such as "look for fever, shock, hypovolemic, hypoxia, abnormal electrolytes, drug ingestion, pneumothorax and cardiac tamponade."

Where the diagnosis is SVT, the defibrillator could ask whether rapid vscular access was available. If access is available, then the defibrillator could prompt the rescuer to consider sedation followed by adenosine (0.1–0.2 mg/kg) followed by rapid normal saline (2–5 ml bolus). If the adenosine fails to convert the rhythm, then the defibrillator may deliver synchronized cardioversion.

If access is not available, then the defibrillator should immediately deliver synchronized cardioversion.

Where the diagnosis is VT, the defibrillator could again ask whether rapid vascular access is available. Where access is not available, the defibrillator could begin delivering synchronized cardioversion as discussed above for SVT. Where access is available, the defibrillator could prompt the rescuer to deliver lidocaine (1 mg/kg), a sedation/analgesic followed by synchronized cardioversion.

If, during the tachycardia 580 treatment protocol, the defibrillator determines that the condition of the victim has changed, the defibrillator will cease prompting the rescuer to deliver the current treatment protocol, and will being prompting the rescuer to deliver a new treatment protocol based on the changed diagnosis. Such a change in protocol may be preceded by a warning to the operator, such as "the patient's condition has changed, begin providing treatment for . . . . "

Where the defibrillator has determined that the appropriate diagnosis is VF or shockable VT 584, the defibrillator could prompt the rescuer to "provide treatment for VF or shockable VT." Alternatively, the defibrillator could provide more detailed instructions such as "continue CPR, secure airway, hyperventilate with oxygen, obtain VI or IO access."Thereafter, the defibrillator would revert to prompting the rescuer to deliver a CPR:shock protocol, such as the ones described in detail above and shown in FIGS. 3–15.

Additional, the defibrillator could prompt the rescuer to administer epinephrine (0.01 mg/kg) following the first series of shocks and then administer lidocaine (1 mg/kg) after each additional defibrillator shock. A counter or timer on the defibrillator controller could monitor the amount of time since the last epinephrine dose and prompt the rescuer to deliver subsequent doses at 3–5 minutes intervals.

If, during the VF or shockable VT 534 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . ."

Where the defibrillator has determined that the appropriate diagnosis is PEA 586, the defibrillator could prompt the rescuer to "provide treatment for PEA." Alternatively, the defibrillator could provide more detailed instructions such as "identify and treat causes for PEA." More detailed information about the causes could also be provided, such as "look for severe hypoxemia, severe acidosis, severe hypovolvemia, tension pneomothorax, cardiac tamponade or profound hypothermia." The prompts could be repeated once followed by a pause to allow the rescuer to perform the action, or could pause until the rescuer indicates either vocally, or by pressing a button, that the procedure has been completed and the rescuer is ready for the next prompt. Following the initial prompts, the defibrillator could instruct the rescuer to consider possible causes. Alternatively, the defibrillator could assess the information provided by the data gatherers to determine possible causes.

Where the defibrillator or the operator are unable to determine a cause for PEA, the defibrillator may prompt the user to "continue CPR, secure airway, hyperventilate with 100% oxygen—obtain IV/IO access." Once IV/IO access has been obtained, the defibrillator could prompt the rescuer to administer epinephrine (0.01 mg/kg first dose, 0.1 mg/kg subsequent doses). As described above, a counter or timer on the defibrillator controller could monitor the amount of time since the last epinephrine dose and prompt the rescuer to deliver subsequent doses at 3–5 minute intervals.

If, during the PEA 586 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . . "

Where the defibrillator has determined that the appropriate diagnosis is asystole 588, the defibrillator could prompt the rescuer to "provide treatment for asystole." Alternatively, the defibrillator may prompt the user to "continue CPR, secure airway, hyperventilate with 100% oxygen—obtain IV/IO access." Once IV/IO access has been obtained, the defibrillator could prompt the rescuer to administer epinephrine (0.01 mg/kg first dose, 0.1 mg/kg subsequent doses). As described above, a counter or timer on the defibrillator controller could monitor the amount of time since the last epinephrine dose and prompt the rescuer to deliver subsequent doses at 3–5 minute intervals.

If, during the asystole 588 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . . "

When the defibrillator has determined that there is normal cardiac function 590, the defibrillator could prompt the rescuer to "place the victim in the rescue position if there is no trauma."

I, during the normal cardiac function 590 treatment protocol, the defibrillator determines that the condition of the victim has changed, the defibrillator will cease prompting the rescuer to deliver the current treatment protocol, and will begin prompting the rescuer to deliver a new treatment protocol based on the changed diagnosis. Such a change in protocol may be preceded by a warning to the operator, such as "the patient's condition has changed, begin providing treatment for . . . . "

Instructions may appear on a visual image generator 24, or may be audible from an audible sound generator 26, or a combination of the two. For the CPR prompts shown in FIGS. 3–15, the visual prompt may consist of, for example, a flashing image of hands compressing a chest at the rate at which the compression should be performed, followed by a flashing image of, for example, lungs inflating at the rate of which the inflations should be performed. Alternating between the two images according to the pre-programmed protocol. Alternatively, the visual prompt may consist of, for example, a flashing image of the word "compress", "thrust" or "press" , followed by the flashing image of the word "breathe", "inflate" or "ventilate". The selection of verbiage may be tailored to the level of experience of the rescuer. As with the graphic representations, the flashing images of the words would be at a rate corresponding to the rate at which the task should be performed.

Alternatively, where the visual image is coordinated with the audible prompt, the visual image may not flash. Also, where the visual image consists of a written prompt, the instructions may be programmed in languages other than English, for example, French, German, Italian, or Japanese. Where the visual image flashes, the rate of flashing of the visual prompt may correspond to the timing at which the step, such as CPR, is to be performed and may be synchronized with the delivery of the audible prompt.

In place of, or in addition to, the visual prompt, an audible prompt may be provided. The prompt is generated by the audible prompt generator 26. The audible prompt may consist of, for example, a time keeping tone for use in CPR prompting which provides, for example, a short pulse tone for compressions and long pulse tone for breathing. Alternating between the two according to a pre-programmed protocol for a period of, for example, one minute. Such a time keeping tone could be produced by, for example, a metronome. Devices for producing a time keeping tone are known in the art. Such devices include: a piezo buzzer, a recording of a tone or tones stored in the ROM, and the like.

Alternatively, the audible prompt for CPR may consist of a voice prompt consisting of, for example, a recorded or synthetically produced verbal instruction such as "thrust" or "press" followed by "breathe" or "inflate", which is repeated at the rate at which CPR is to be performed. For example, the defibrillator programmed to follow the AHA protocol for a child (shown in FIG. 6, steps 222 B to 222 C), could issue the synchronized command "thrust . . . thrust . . . thrust . . . thrust . . . thrust . . . breathe . . ." which is repeated for a period of one minute.

Instead, the audible prompt for CPR may consist of an instruction to, for example, "administer two breaths", followed by "administer 15 compressions". Where the prompt is followed by a pause, each instruction would be followed by an appropriate length pause for performing that instruction. Alternatively, following the command, a timing tone could be provided that assists the rescuer in executing the command at the appropriate time interval. For example, referring back to the AHA CPR protocol for a child shown in FIG. 6, 222 B to 222 C, the instruction could be issued as follows: "Deliver 5 compression . . . (timing tone) (timing tone) . . . (timing tone) . . . (timing tone) . . . (timing tone) . . . deliver one breath . . . (timing tone)."

The audible prompts may be synchronized with any visual prompts that are provided such that the corresponding visual prompt appears when the audible prompt begins providing instructions for a particular CPR or ACLS step. Alternatively, the audible prompt may be synchronized with the visual prompt such that the visual prompt will flash the instruction at the same time the audible prompt provides the instruction.

Additional prompting may be included that responds to a rescuers request for help. Such prompting would be similar to a "help" button found on a personal computer. The additional prompting may provide more detailed instructions to the rescuer such as dosage recommendations for pharmacological agents, contraindications, or may provide an additional explanation of the step. Such additional information would be particularly useful for defibrillator that are used in training. For example, when the defibrillator requests information from the rescuer, an explanation of how or where to obtain the information might be provided when the rescuer indicates the need for "help".

As with the CPR prompting, audible and/or visible prompting may be used to guide a rescuer in treating a victim based on each of the diagnosis possibilities. Other combinations of audible prompting (both verbal and tonal)

with visual prompting (both written and graphical) are within the scope of the invention, although not specifically set forth in detail herein.

It should be appreciated that the scope of the invention is not limited to the embodiments described above. Various modifications and alterations might be made by those skilled in the art without departing from the spirit and scope of the present invention.

What is claimed is:

1. A defibrillator comprising an energy source, an electrode interface, a controller, and an audible sound generator, wherein the defibrillator analyzes a heart rhythm, and provides a synchronized audible prompts to instruct a rescuer in delivering CPR on a patient, wherein the prompts comprise detailed instructions.

2. The defibrillator of claim 1 wherein the synchronized CPR prompts are audible prompts.

3. The defibrillator of claim 2 wherein the audible prompts are verbal.

4. The defibrillator of claim 2 wherein the audible prompts are tonal.

5. The defibrillator of claim 1 wherein the synchronized CPR prompts are for performing CPR on a child.

6. The defibrillator of claim 1 wherein the synchronized CPR prompts are for performing CPR on an adult.

7. A defibrillator comprising an energy source, an electrode interface, a controller, and a visual image generator, wherein the defibrillator analyzes a heart rhythm, and provides synchronized visual prompts and detailed audio instruction to instruct a rescuer in delivering CPR at a rate corresponding to the synchronized prompts.

8. The defibrillator of claim 7 wherein the defibrillator is capable of generating audible sound.

9. The defibrillator of claim 7 wherein the synchronized CPR prompts are visual prompts.

10. The defibrillator of claim 9 wherein the visual prompts are graphic images.

11. The defibrillator of claim 10 wherein separate graphic images are provided for chest compression of and rescue breathing steps.

12. The defibrillator of claim 11 wherein the visual prompts flash at a predetermined rate.

13. The defibrillator of claim 8 wherein the synchronized CPR prompts are audible prompts.

14. The defibrillator of claim 13 wherein the audible prompts are verbal.

15. The defibrillator of claim 13 wherein the audible prompts are tonal.

16. The defibrillator of claim 13 wherein the audible prompts are emitted at a predetermined rate.

17. The defibrillator of claim 13 where the audible prompts are synchronized with visual images.

18. The defibrillator of claim 13 wherein the visual images are timed to correspond with audible prompts.

19. The defibrillator of claim 7 wherein the instructions are for performing CPR on a child.

20. The defibrillator of claim 7 wherein the instructions are for performing CPR on an adult.

21. A defibrillator comprising:
    a defibrillator, the defibrillator comprising an energy source, an electrode interface and an audible sound generator, wherein the electrode interface is in electrical communication with the energy source to provide electrotherapy to a patient;
    a CPR instruction generator communicating with the audible sound generator; and
    an ACLS instruction generator communicating with the audible sound generator;
    wherein the CPR instruction generator generates synchronized prompts during delivery of CPR to instruct a rescuer in delivering CPR at a rate corresponding to the synchronized prompts, the synchronized prompts comprising detailed CPR instructions.

22. The defibrillator system of claim 21 wherein the audible sound generator generates audible prompts in response to instructions from the ACLS instruction generator.

23. The defibrillator system of claim 22 wherein the audible prompts are verbal.

24. The defibrillator system of claim 22 wherein the audible prompts are tonal.

25. The defibrillator system of claim 22 wherein the audible prompts are emitted at a predetermined rate.

26. The defibrillator system of claim 22 wherein the defibrillator has a visual image generator.

27. The defibrillator system of claim 26 wherein the ACLS instruction generator communications with the visual image generator.

28. The defibrillator system of claim 26 wherein the visual image generator generates visual prompts.

29. The defibrillator system of claim 28 wherein the visual prompts are graphic images.

30. The defibrillator of claim 21 wherein the instructions are for performing CPR on a child.

31. The defibrillator of claim 21 wherein the instructions are for performing CPR on an adult.

32. The defibrillator of claim 1 further comprising a data gatherer and wherein
    if the patient is conscious, said data gatherer monitors at least one patient dependent parameter and the defibrillator delivers a first set of instructions to a patient caregiver; or
    if the patient is unconscious, said data gatherer monitors at least one patient dependent parameter and the defibrillator delivers a second set of instructions to the patient caregiver for treatment of an unconscious patient.

33. The defibrillator of claim 32 wherein the patient dependent parameter is selected from the group consisting of: ECG, pulse, pulse oximetry, and blood pressure.

34. The defibrillator of claim 2 further comprising a data gatherer and wherein
    if the patient is conscious, said data gatherer monitors at least one patient dependent parameter and the defibrillator delivers a first set of instructions to a patient caregiver; or
    if the patient is unconscious, said data gatherer monitors at least one patient dependent parameter and the defibrillator delivers a second set of instructions to the patient caregiver for treatment of an unconscious patient.

35. The defibrillator of claim 34 wherein patient dependent parameters are selected from the group consisting of: ECG, pulse, pulse oximetry, and blood pressure.

36. A method of treating a patient using a defibrillator wherein if the patient is conscious, monitor at least one patient dependent parameter and deliver a first set of instructions to a patient caregiver; or if the patient is unconscious, monitor at least one patient dependent parameter and deliver a second set of instructions to the patient caregiver for treatment of an unconscious patient.

37. The method of claim 36 wherein patient dependent parameters are selected from the group consisting of ECG, pulse oximetry, and blood pressure.

38. The method of claim 37 wherein the first set of instructions are selected from the group consisting of: normal cardiac function, tachyarrhythmia, acute myocardial infarction, and bradycardia.

39. The method of claim 37 wherein the second set of instructions are selected from the group consisting of: pulse less electrical activity, asystole, ventricular fibrillation, and shockable ventricular tachycardia.

* * * * *